United States Patent
Schumacher et al.

(10) Patent No.: US 9,260,584 B2
(45) Date of Patent: Feb. 16, 2016

(54) COATED, WET-CHEMICALLY OXIDIZED ALUMINUM EFFECT PIGMENTS, METHOD FOR THE PRODUCTION THEREOF, COATING AGENT AND COATED OBJECT

(71) Applicant: Eckart GmbH, Hartenstein (DE)

(72) Inventors: Dirk Schumacher, Pegnitz (DE); Michael Gruener, Auerbach (DE); Sebastian Hoefener, Nuremberg (DE); Oliver Struck, Henfenfeld (DE)

(73) Assignee: Eckart GmBH (DE)

( * ) Notice: Subject to any disclaimer, the term of this patent is extended or adjusted under 35 U.S.C. 154(b) by 0 days.

(21) Appl. No.: 14/355,984

(22) PCT Filed: Nov. 2, 2012

(86) PCT No.: PCT/EP2012/071735
§ 371 (c)(1),
(2) Date: May 2, 2014

(87) PCT Pub. No.: WO2013/064643
PCT Pub. Date: May 10, 2013

(65) Prior Publication Data
US 2015/0098972 A1    Apr. 9, 2015

(30) Foreign Application Priority Data

Nov. 4, 2011 (DE) .......... 10 2011 055 072

(51) Int. Cl.
| | |
|---|---|
| C09C 1/64 | (2006.01) |
| C08K 9/02 | (2006.01) |
| C09D 5/36 | (2006.01) |
| C08K 3/22 | (2006.01) |
| A61K 8/26 | (2006.01) |
| A61Q 1/06 | (2006.01) |
| A61Q 1/10 | (2006.01) |
| A61Q 3/02 | (2006.01) |
| A61K 8/02 | (2006.01) |
| C09D 5/03 | (2006.01) |
| A61K 8/25 | (2006.01) |
| A61K 8/81 | (2006.01) |
| A61Q 1/00 | (2006.01) |
| A61Q 1/04 | (2006.01) |
| A61Q 5/00 | (2006.01) |
| A61Q 19/00 | (2006.01) |
| A61Q 19/10 | (2006.01) |
| C08K 3/36 | (2006.01) |
| C09D 133/14 | (2006.01) |
| C08L 27/16 | (2006.01) |
| A61Q 5/06 | (2006.01) |

(52) U.S. Cl.
CPC ............. *C08K 3/22* (2013.01); *A61K 8/0266* (2013.01); *A61K 8/25* (2013.01); *A61K 8/26* (2013.01); *A61K 8/8152* (2013.01); *A61Q 1/00* (2013.01); *A61Q 1/04* (2013.01); *A61Q 1/06* (2013.01); *A61Q 1/10* (2013.01); *A61Q 3/02* (2013.01); *A61Q 5/00* (2013.01); *A61Q 19/007* (2013.01); *A61Q 19/10* (2013.01); *C08K 3/36* (2013.01); *C09C 1/648* (2013.01); *C09D 5/035* (2013.01); *C09D 133/14* (2013.01); *A61K 2800/10* (2013.01); *A61K 2800/43* (2013.01); *A61K 2800/63* (2013.01); *A61K 2800/651* (2013.01); *A61Q 5/06* (2013.01); *A61Q 5/065* (2013.01); *C01P 2004/03* (2013.01); *C01P 2004/51* (2013.01); *C01P 2004/54* (2013.01); *C01P 2004/61* (2013.01); *C01P 2004/86* (2013.01); *C01P 2006/12* (2013.01); *C08K 9/02* (2013.01); *C08K 2003/2227* (2013.01); *C08L 27/16* (2013.01); *C09C 2200/1004* (2013.01); *C09C 2200/405* (2013.01); *C09C 2220/106* (2013.01); *C09D 5/36* (2013.01)

(58) Field of Classification Search
CPC .......... C09C 1/648; C09D 5/035; C09D 5/36; C09D 133/14; C08K 3/22; C08K 3/36; C08K 9/02; C08L 22/16
USPC ....................................... 106/404
See application file for complete search history.

(56) References Cited

U.S. PATENT DOCUMENTS

| | | | | | |
|---|---|---|---|---|---|
| 4,544,415 | A | * | 10/1985 | Franz et al. | ........... 106/417 |
| 5,277,711 | A | * | 1/1994 | Schmidt et al. | ........... 106/404 |

(Continued)

FOREIGN PATENT DOCUMENTS

| | | |
|---|---|---|
| DE | 19820112 A1 | 11/1999 |
| DE | 10354763 A1 | 6/2005 |

(Continued)

OTHER PUBLICATIONS

Li et al "Aluminum Pigments Encapsulated by Inorganic-Organic Hybrid Coatings and Their Stability in Alkaline Aqueous Media", J. Coat. Technol. Res., 5 (1) 77-87, 2008.*

(Continued)

*Primary Examiner* — Anthony J Green
(74) *Attorney, Agent, or Firm* — The Webb Law Firm, P.C.

(57) ABSTRACT

A coated wet-chemically oxidized aluminum effect pigment is provided having at least one metal oxide layer having at least one metal oxide which differs from aluminum oxide and an enveloping organic polymer layer, wherein the weight ratio of the metal oxide of the metal oxide layer to aluminum oxide in the wet-chemically produced aluminum oxide layer of uncoated wet-chemically oxidized aluminum effect pigment is in a range of from 1:1 to 1:40. Also, a method for the production of the pigment is provided.

19 Claims, 8 Drawing Sheets

(56) References Cited

U.S. PATENT DOCUMENTS

| | | | |
|---|---|---|---|
| 5,332,767 A | 7/1994 | Reisser et al. | |
| 5,607,504 A * | 3/1997 | Schmid et al. | 106/403 |
| 5,931,996 A | 8/1999 | Reisser et al. | |
| 5,964,936 A * | 10/1999 | Reisser | 106/404 |
| 6,013,370 A * | 1/2000 | Coulter et al. | 428/403 |
| 6,761,762 B1 | 7/2004 | Greiwe et al. | |
| 6,776,835 B2 * | 8/2004 | Andes et al. | 106/415 |
| 7,300,510 B2 * | 11/2007 | Seeger et al. | 106/401 |
| 7,828,890 B2 * | 11/2010 | Henglein et al. | 106/404 |
| 8,129,021 B2 * | 3/2012 | Kaupp et al. | 428/403 |
| 2002/0041047 A1 * | 4/2002 | Josephy et al. | 264/81 |
| 2004/0123779 A1 * | 7/2004 | Bagala et al. | 106/415 |
| 2004/0226480 A1 | 11/2004 | Greiwe et al. | |
| 2005/0120917 A1 * | 6/2005 | Ruger et al. | 106/415 |
| 2005/0204958 A1 * | 9/2005 | Kuebelbeck et al. | 106/403 |
| 2007/0104663 A1 | 5/2007 | Henglein et al. | |
| 2007/0199478 A1 * | 8/2007 | Schlegl et al. | 106/404 |
| 2007/0243149 A1 | 10/2007 | Hofacker et al. | |
| 2008/0087187 A1 | 4/2008 | Maul et al. | |
| 2008/0115693 A1 | 5/2008 | Hashizume | |
| 2008/0249209 A1 | 10/2008 | Trummer et al. | |
| 2009/0117281 A1 | 5/2009 | Sato et al. | |
| 2009/0264575 A1 | 10/2009 | Henglein et al. | |
| 2010/0152355 A1 | 6/2010 | Schumacher et al. | |
| 2010/0194836 A1 * | 8/2010 | Prolss et al. | 106/404 |
| 2010/0269733 A1 * | 10/2010 | Kremitzl | 106/404 |
| 2011/0160389 A1 * | 6/2011 | Bubat et al. | 524/588 |
| 2011/0179971 A1 | 7/2011 | Proelss et al. | |
| 2011/0197782 A1 | 8/2011 | Wang et al. | |
| 2011/0265690 A1 * | 11/2011 | Schumacher et al. | 106/417 |
| 2012/0274714 A2 * | 11/2012 | Prolss et al. | 347/100 |
| 2013/0035400 A1 * | 2/2013 | Nguyen et al. | 514/770 |

FOREIGN PATENT DOCUMENTS

| | | | | |
|---|---|---|---|---|
| DE | 10361437 A1 | 7/2005 | | |
| DE | 102004026955 A1 | 12/2005 | | |
| EP | 1619222 A1 * | 1/2006 | | C09C 1/64 |
| WO | WO 2004/092284 A1 * | 10/2004 | | C09C 1/00 |
| WO | 2005063897 A2 | 7/2005 | | |
| WO | 2006041658 A1 | 4/2006 | | |
| WO | WO 2006/041658 A1 * | 4/2006 | | C09C 1/64 |
| WO | 2007115675 A2 | 10/2007 | | |
| WO | 2008095697 A1 | 8/2008 | | |
| WO | 2009152941 A2 | 12/2009 | | |

OTHER PUBLICATIONS

Albrecht et al., "Glitzern in optischer Tiefe", Farbe und Lack, 2008, S. 52-56, vol. 9.
Albrecht et al., "Sparkling with optical depth", PPCJ, Dec. 2008, 3 pages.
Albrecht et al., Sparkling with optical depth, Powder Coatings Yearbook, 2009, 18-22.

* cited by examiner

1μm

1μm

1μm

1μm

US 9,260,584 B2

COATED, WET-CHEMICALLY OXIDIZED ALUMINUM EFFECT PIGMENTS, METHOD FOR THE PRODUCTION THEREOF, COATING AGENT AND COATED OBJECT

CROSS-REFERENCE TO RELATED APPLICATIONS

This application is the United States national phase of International Application No. PCT/EP2012/071735 filed Nov. 2, 2012, and claims priority to German Patent Application No. 10 2011 055 072.0, filed Nov. 4, 2011, the disclosures of which are hereby incorporated in their entirety by reference.

BACKGROUND OF THE INVENTION

1. Field of the Invention

The invention relates to colored oxidized aluminum effect pigments, a method for their production and the use thereof. The invention furthermore relates to a coating agent and a coated object.

2. Description of Related Art

Aluminum effect pigments offer a large number of possible uses and are established in diverse fields of use. They are often to be encountered, for example, in cosmetics, in the automobile sector, in the production of plastics, in paints or the printing industry. In addition to optical properties, they also offer, for example, specific technical properties here. Due to their platelet-shaped form, aluminum effect pigments display interesting optical effects, which is to be attributed to their larger reflective surface. In addition to the basic shape of the effect pigments per se, various surface modifications have furthermore been developed in the past in order to create new properties or to influence the existing properties in a targeted manner.

For example, U.S. Pat. No. 5,964,936 A describes a controlled wet-chemical oxidation of the surface of aluminum effect pigments, which are marketed by Eckert under the name Aloxal. A characteristic surface structure forms here, which brings about a coloring of the effect pigments as a consequence of interference effects. Although the champagne color shades, for example, which can be achieved by this means offer a highly interesting color spectrum for many uses, the water contained in the aluminum oxide layer can bring about a subsequent oxidation, with the result that a long-term color stability can be achieved only with difficulty.

U.S. Pat. No. 5,931,996 A describes a method for the production of colored aluminum effect pigments, wherein color pigments are introduced into a metal oxide coating of the aluminum effect pigments.

US 2007/0104663 A1 furthermore describes the coating of wet-chemically oxidized aluminum particles with a metal chalcogenide layer. Particles obtained here have a minimal total thickness and firmly adhering oxide layers, and are acceptable in terms of safety.

US 2008/0249209 A1 moreover describes the production of inorganic/organic mixed layers having an inorganic network and at least one organic component. It has been found that the production of such inorganic/organic mixed layers is elaborate in terms of process technology.

Known from US 2009/0264575 A1 are metal effect pigments having a coating which contains oligomeric and/or polymeric binders which are chemically crosslinkable and/or can be crosslinked under the action of heat, IR radiation, UV radiation and/or electron beams.

U.S. Pat. No. 6,761,762 B1 discloses effect pigments coated with reactive orientation aids. The subject of this patent is constituted substantially by aluminum effect pigments which can be coated with a coating of metal oxides or polymers. Orientation aids which make possible a covalent binding to the binder of a paint or a varnish are then arranged on this coating.

Finally, metal effect pigments, in particular aluminum effect pigments, coated with synthetic resin are known from U.S. Pat. No. 5,332,767 A.

US 2009/0117281 A1 describes aluminum effect pigments comprising an adhesion promotion layer and a polymer layer. The aim here is to be an improved water resistance and chemical resistance of the pigments.

US 2010/0152355 A1 furthermore describes metal effect pigments which are provided with a synthetic resin coating, wherein the synthetic resin coating comprises a polymer and an organofunctional silane.

SUMMARY OF THE INVENTION

None of the abovementioned documents relates to the problem of an after-oxidation in wet-chemically oxidized aluminum pigments. In the present case the term "after-oxidation" denotes an uncontrolled oxidation process which follows the wet-chemical oxidation and is presumably to be attributed to the water bonded on or in the wet-chemically produced aluminum oxide layer.

It has furthermore been shown that, when wet-chemically oxidized aluminum effect pigments are used in particular in automobile varnish formulations, bubbles or similar irregularities, so-called popping blisters or also pops, can occur during stoving of the corresponding varnish coatings, as a result of which the optical and/or functional properties of the varnish are drastically impaired. A similar adverse effect also occurs in plastics materials when wet-chemically oxidized aluminum effect pigments are used. Thus, for example, during extrusion of thermoplastics which contain wet-chemically oxidized aluminum effect pigments a clouding is observed, which impairs the optical properties of the plastic. It is believed that this clouding is also to be attributed to the formation of gas bubbles in the plastic.

In particular, the abovementioned documents give no indications of what measures would have to be taken so that the optical properties of wet-chemically oxidized aluminum pigments are not subject to changes over time.

In some non-limiting embodiments, there is provided a coated wet-chemically oxidized aluminum effect pigment comprising:

at least one metal oxide layer comprising at least one metal oxide which differs from aluminum oxide; and at least one enveloping organic polymer layer, wherein the weight ratio of the metal oxide of the at least one metal oxide layer to aluminum oxide in a wet-chemically produced aluminum oxide layer of uncoated wet-chemically oxidized aluminum effect pigment is in a range of from 1:1 to 1:40.

Also provided is a method for the production of a coated wet-chemically oxidized aluminum effect pigment, wherein the method comprises the following steps:

(1) wet-chemical oxidation of an aluminum effect pigment, (2) coating of the wet-chemically oxidized aluminum effect pigment obtained in step (1) with metal oxide which differs from aluminum oxide, wherein the weight ratio of the metal oxide, applied as at least one metal oxide layer, to the aluminum oxide layer wet-chemically produced in step (1) is in a range of from 1:1 to 1:40, and (3) coating of the wet-chemically oxidized aluminum effect pigment, coated with metal oxide and obtained in step (2), with at least one enveloping organic polymer layer.

Also provided are preparations, such as coating compositions and objects, comprising the coated wet-chemically oxidized aluminum effect pigment.

The object of the invention is consequently to provide wet-chemically oxidized aluminum effect pigments, the optical properties of which do not change over time, which in particular have a color stability, make possible a simple and diverse application and at the same time show no noticeable losses with respect to the optical quality.

An object of the present invention is furthermore to provide a method for the production of such pigments.

An object of the present invention is furthermore to provide uses in which the pigments according to the invention can be particularly advantageously utilized.

The object forming the basis of the invention is achieved by the provision of wet-chemically oxidized aluminum effect pigments, wherein the wet-chemically oxidized aluminum effect pigments have at least one metal oxide layer which differs from aluminum oxide and at least one enveloping organic polymer layer, and wherein the weight ratio of the metal oxide, which differs from aluminum oxide and is applied as metal oxide layer, to the wet-chemically produced aluminum oxide layer is in a range of from 1:1 to 1:40, preferably in a range of from 1:2 to 1:25.

In further embodiments of the abovementioned pigments, the sum of the contents of the at least one metal oxide layer and the at least one organic polymer layer is in a range of from 10 to 50 wt.-%, relative to the weight of the uncoated, wet-chemically oxidized aluminum effect pigment, and the weight ratio of the at least one metal oxide layer which differs from aluminum oxide to the at least one polymer layer is in a range of from 1:2 to 1:20. In particular, in preferred ones of the abovementioned embodiments it is preferred that the sum of the contents of the at least one metal oxide layer and the at least one organic polymer layer is in a range of from 13 to 40 wt.-%, relative to the weight of the uncoated, wet-chemically oxidized aluminum effect pigment, and the weight ratio of the at least one metal oxide layer which differs from aluminum oxide to the at least one polymer layer is in a range of from 1:2.2 to 1:17.

In further embodiments of the abovementioned pigments, the elemental aluminum content is at most 87 wt.-%, relative to the weight of the uncoated, wet-chemically oxidized aluminum effect pigments.

In further embodiments of the abovementioned pigments, the weight proportion of the at least one metal oxide layer which differs from aluminum oxide is at least 0.8 wt.-%, relative to the weight of the uncoated, wet-chemically oxidized aluminum effect pigments. Furthermore, in further embodiments of the abovementioned pigments it is preferred that the weight proportion of the at least one metal oxide layer which differs from aluminum oxide is at most 20 wt.-%, relative to the weight of the uncoated, wet-chemically oxidized aluminum effect pigments. In others of the abovementioned embodiments of the abovementioned pigments, the weight proportion of the at least one metal oxide layer which differs from aluminum oxide is in a range of from 0.8 to 20 wt.-%, preferably in a range of from 1.6 to 16 wt.-% and still more preferably in a range of from 2.1 to 14 wt.-%, relative to the weight of the uncoated, wet-chemically oxidized aluminum effect pigments.

In further embodiments of the abovementioned pigments, the at least one metal oxide layer which differs from aluminum oxide substantially consists of metal oxide which is selected from the group consisting of silicon oxide, boron oxide, zirconium oxide, cerium oxide, iron oxide, titanium oxide, chromium oxide, tin oxide, molybdenum oxide, oxide hydrates thereof, hydroxides thereof and mixtures thereof. In particular, the at least one metal oxide layer of the abovementioned pigments which differs from aluminum oxide substantially consists of silicon oxide, hydroxides thereof or mixtures thereof.

In further embodiments of the abovementioned pigments, the weight proportion of the at least one organic polymer layer is at least 8 wt.-%, relative to the weight of the uncoated, wet-chemically oxidized aluminum effect pigment. In further embodiments of the abovementioned pigments, the weight proportion of the at least one organic polymer layer is at most 40 wt.-%, relative to the weight of the uncoated, wet-chemically oxidized aluminum effect pigment. In others of the abovementioned embodiments, the weight proportion of the at least one organic polymer layer is in a range of from 8 to 40 wt.-%, relative to the weight of the uncoated, wet-chemically oxidized aluminum effect pigment.

In further embodiments of the abovementioned pigments, the at least one organic polymer of the at least one organic polymer layer is selected from the group consisting of polyacrylate, polymethacrylate, polyacrylamide, polyacrylonitrile, polyvinyl chloride, polyvinyl acetate, polyamide, polyalkene, polydiene, polyalkyne, polyalkylene glycol, epoxy resin, polyester, polyether, polyol, polyurethane, polycarbonate, polyethylene terephthalate and mixtures thereof, in particular from the group consisting of polyacrylate, polymethacrylate and mixtures thereof.

In further embodiments of the abovementioned pigments, the at least one metal oxide layer which differs from aluminum oxide is not an inorganic/organic mixed layer.

In further embodiments of the abovementioned pigments, the non-oxidized aluminum of the aluminum effect pigments according to the invention has a purity of at least 99.5 wt.-%. In other embodiments of the present invention, the non-oxidized aluminum of the aluminum effect pigments according to the invention on the other hand consists of an aluminum alloy which contains at least 5 wt.-% other metals in addition to aluminum. The other metals here are preferably selected from the group consisting of iron, manganese, copper, vanadium, chromium, nickel, cobalt, silicon, magnesium, zinc and titanium.

In further embodiments, the abovementioned pigments have a high refractive index metal chalcogenide layer, preferably a high refractive index metal oxide layer, such as, for example, iron oxide, in addition to the at least one metal oxide layer which differs from aluminum oxide.

The present invention furthermore relates to the provision of a method for the production of coated wet-chemically oxidized aluminum effect pigments, wherein the method comprises the following steps:

(1) wet-chemical oxidation of aluminum effect pigments,
(2) coating of the wet-chemically oxidized aluminum effect pigments obtained in step (1) with metal oxide which differs from aluminum oxide, wherein the weight ratio of the metal oxide, applied as at least one metal oxide layer, to the aluminum oxide layer wet-chemically produced in step (1) is in a range of from 1:1 to 1:40,
(3) coating of the wet-chemically oxidized aluminum effect pigments, coated with metal oxide and obtained in step (2), with at least one enveloping organic polymer layer.

In particular, in further embodiments it is preferred that the metal oxide is applied with a sol-gel process in step 2.

In further embodiments, it is preferred that the wet-chemical oxidation in step 1 is carried out at pH 7 to 12 with a mixture of water and one or more water-miscible solvents. Examples of such water-miscible solvents are ethanol, n-propanol, propanol, n-butanol, i-butanol, methoxypropanol, acetone and butyl glycol.

The present invention furthermore relates to pigments which have been produced using the methods according to the invention.

The present invention furthermore relates to the use of the pigments according to the invention in plastic, cosmetics or in a coating agent, in particular a paint, a varnish, a powder coating or a printer ink. The pigment according to the invention can also be added to a medium in order to achieve a specific technical effect, wherein optical effects are not included. An example of this is the use of the pigment according to the invention in a plastic as a laser marking additive. The pigment according to the invention can of course also be used in order to influence or configure the optical properties of a medium. Examples of this are pigments which bring about a change in color as a consequence of their intrinsic color or on the basis of interference effects.

The present invention furthermore relates to a coating agent which contains the pigments according to the invention.

In addition, the present invention relates to coated objects which contain and/or feature the pigments according to the invention and/or the coating agent according to the invention.

BRIEF DESCRIPTION OF THE DRAWINGS

The foregoing summary, as well as the following detailed description, will be better understood when read in conjunction with the appended drawings. In the drawings.

DETAILED DESCRIPTION

The production of colored aluminum effect pigments by wet-chemical oxidation of aluminum effect pigments is already known from U.S. Pat. No. 5,964,936 A. The pigments obtained here can have the abovementioned problem that they are subject to an after-oxidation, as a consequence of which a change in color of the pigments in question occurs. However, such a change in color is unacceptable in many fields. For example, in the repair varnish systems of the automobile industry slight changes in color are already unacceptable. Since wet-chemically oxidized aluminum pigments cause trouble in many uses, for example by the formation of bubbles in a coating agent, such as a varnish or a paint, in the past the wet-chemically oxidized aluminum effect pigments could not be used in many fields. The imitation of the specific color shades and the particular optical qualities of the wet-chemically oxidized aluminum effect pigments was very difficult in terms of process technology.

It has been found, surprisingly, that by the application of at least one metal oxide layer and at least one organic polymer layer durably color-stable aluminum effect pigments can be produced simply in terms of process technology and new fields of use for wet-chemically oxidized aluminum effect pigments can therefore be opened up.

It has furthermore been found, surprisingly, that particularly advantageous aluminum effect pigments are obtained by the application of at least one, preferably a single, metal oxide layer which differs from aluminum oxide to the wet-chemically oxidized aluminum effect pigments. It is believed that the problems of a subsequent oxidation are substantially to be attributed to the water bonded on or in the wet-chemically produced aluminum oxide layer. Measurements have thus shown, for example, that due to storage under room atmosphere before the wet-chemical oxidation, approx. 0.4 wt.-% water is present on the aluminum effect pigments used in the wet-chemical oxidation. After the wet-chemical oxidation, on the other hand, a water content of 8.1 wt.-%, in each case relative to the total weight of the respective aluminum effect pigments, is found on these aluminum effect pigments.

Figure 1:
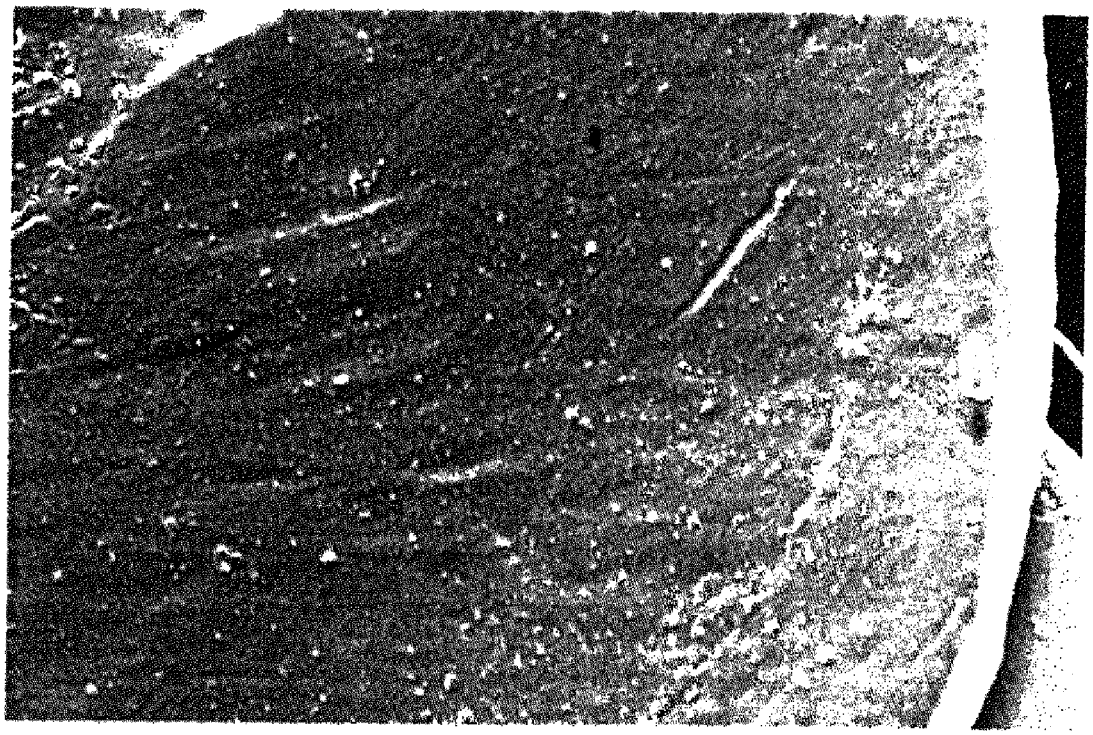
FIG. 1 shows an SEM analysis of an aluminum effect pigment, such as is used, for example, in Example 2, before the wet-chemical oxidation. Only traces of abrasion and very fine particles are to be found on the uniformly molded surface.

The wet-chemically produced aluminum oxide layer does not form a dense and closed structure such as is known of a natural aluminum oxide layer. As can be seen, for example, from FIG. 9, the wet-chemically produced aluminum oxide layer forms a porous structure, which is additionally permeated by channels. This is also demonstrated, for example, by measurements of the BET surface area, according to which the BET surface area of customary aluminum effect pigments of the type shown in FIG. 1 increases from 2.6 $m^2/g$ to 35.4 $m^2/g$ as a consequence of the wet-chemical oxidation. FIGS. 2, 4, 6, 7, 8 and 9 show SEM photographs of wet-chemically oxidized aluminum effect pigments.

The application of a metal oxide layer or polymer layer to the surface of the wet-chemically oxidized aluminum effect pigments should accordingly merely lead to the water contained being enclosed and the abovementioned after-oxidation continuing to proceed in an uncontrolled manner.

Without being understood as limiting the invention, the inventors believe that the aluminum surface which is inadequately protected as a consequence of the porous aluminum oxide layer promotes the formation of the subsequently applied metal oxide layer which differs from aluminum oxide at the sites where the water is bonded or embedded, and a first protection against a subsequent oxidation arises hereby. In particular, coating methods for the application of the metal oxide layer in which the metal oxide layer which differs from aluminum oxide is applied by means of a hydrolysis reaction, in particular using the sol-gel process, have furthermore proved to be particularly advantageous. By the term "hydrolysis reaction" in the context of the present invention is meant that the metal oxide source is decomposed with consumption of water. Examples of such hydrolysis reactions are the cleavage of alcoholates into alcohol and metal hydroxide or the cleavage of metal halide into hydrogen halide and metal hydroxide. In particular, by a "hydrolysis reaction" in the context of the invention is meant the cleavage of alcoholates into alcohol and metal hydroxide.

Without being understood as limiting the invention, the inventors believe that due to the abovementioned hydrolysis reactions the water bonded on or in the wet-chemically produced aluminum oxide layer is at least partially, preferably predominantly, further preferably completely, consumed and an after-oxidation is thus effectively impeded or prevented. Surprisingly, small amounts of a metal oxide source are already sufficient for this. In the context of the present invention, the term "metal oxide source" denotes metal-containing starting substances from which the metal oxide coating is produced. Examples of these are, in particular, metal alkoxylates, wherein the alkoxyl group contains one to six carbon atoms, preferably one to three carbon atoms. Tetramethoxysilane and/or tetraethoxysilane have proved to be very suitable. Without being understood as limiting the invention, the inventors believe that the wet-chemically produced aluminum oxide promotes the formation of the metal oxide layer which differs from aluminum oxide possibly on the basis of pH effects or electronic effects and the water bonded on and/or in the wet-chemically produced aluminum oxide layer is therefore preferably consumed. The preferred use of coating methods using a hydrolysis reaction for the application of the metal oxide layer, preferably the sol-gel method, thus makes possible a particularly gentle chemical drying of the wet-chemically produced aluminum oxide layer which would not have been achievable by another route.

A removal of the water which is as gentle as possible is necessary in particular in the case of the wet-chemically oxidized aluminum effect pigments used according to the invention. Thus, due to their rough and as a result large surface area wet-chemically oxidized aluminum effect pigments tend towards agglomeration much more strongly than non-oxidized aluminum effect pigments. In contrast to conventional methods, such as, for example, drying under negative pressure, in the method according to the invention only the small amount of water contained in the organic solvent is consumed and the amount of solvent overall is consequently reduced only minimally. No noticeable concentration of the pigments thus occurs.

Furthermore, in the method according to the invention the fine surface structure is not damaged, such as can take place, for example, in conventional drying methods due to high thermal loads. However, damage to or even destruction of the fine surface structure impairs the optical effect generated by wet-chemical oxidation of the aluminum effect pigments, since the intrinsic color of these pigment particles is brought about by interference effects on just these fine surface structures. Furthermore, the conventional drying methods are very time- and labor-intensive. Conventionally dried aluminum effect pigments produced by wet-chemical oxidation also bond water on contact with air, with the result that storage and processing with exclusion of air and moisture would be necessary in order to avoid an after-oxidation. Alternatively, such pigments could be stored over a longer period of time until an adequate color constancy is achieved as a consequence of a subsequently formed natural aluminum oxide layer. However, this would drastically increase the production time and cause additional storage costs. In addition, such an uncontrolled and uncontrollable after-oxidation would result in a color shade which is difficult to predict and could lower the color brilliance as a consequence of a non-uniform after-oxidation of the pigments.

It has furthermore been shown, surprisingly, that a subsequent release of water in a condensation step, for example in the sol-gel process, is also not harmful. Without being understood as limiting the invention, the inventors believe that the water released, for example, in a subsequent condensation is present in finely dispersed form in the metal oxide layer which differs from aluminum oxide and is forming and formed. Due to the impermeability to water of the metal oxide layer which differs from aluminum oxide, however, the finely dispersed water molecules do not bring about an oxidation of the underlying aluminum. Furthermore, there is evidently no adequately large accumulation of water molecules present which could form gas bubbles when the particles are heated, as a result of which the optical quality of an application medium, for example a paint or a varnish, would be impaired.

In addition, it has been shown, surprisingly, that the aluminum effect pigments according to the invention have further advantages in terms of application technology. For example, the aluminum effect pigments according to the invention have an excellent applicability in the form of a powder coating.

Due to the above-described wet-chemical oxidation of aluminum effect pigments, yellowish color shades in particular, such as champagne-colored color shades, can be obtained. The pigments according to the invention have an excellent gloss. By increasing the degree of oxidation, more intensely colored and darker pigments according to the invention can be obtained. In further embodiments, the metal content of the pigments according to the invention is therefore preferably at most 87 wt.-%, further preferably 85 wt.-%, still further preferably at most 81 wt.-%, more preferably at most 77 wt.-%, still more preferably at most 74 wt.-% and most preferably at most 71 wt.-%, in each case relative to the total weight of the uncoated, wet-chemically oxidized aluminum effect pigments. The metal content is determined, for example, by dissolving the uncoated pigments in 15% aqueous sodium hydroxide solution and quantifying the amount of hydrogen being released.

However, it has furthermore been shown that color shades of lower quality are achieved in aluminum oxide layers which are too thick. Without being understood as limiting the invention, it is the opinion of the inventors that a porous aluminum oxide layer which is too thick does not have an adequate stability and the preferred regular surface structure has ever more damaged spots. This in turn leads to a deterioration in the pigment color. In further embodiments in which, for example, a lighter color is desired for producing a subtle color nuance, it is preferred that the elemental aluminum content in the pigments according to the invention is at least 25 wt.-%, preferably at feast 28 wt.-%, more preferably at least 31 wt.-%, still more preferably at least 34 wt.-% and most preferably at least 36 wt.-%, in each case relative to the total weight of the uncoated, wet-chemically oxidized aluminum effect pigments.

In others of the abovementioned embodiments, the elemental aluminum content in the wet-chemically oxidized aluminum effect pigments used according to the invention is in a range of from 25 to 87 wt.-%, relative to the weight of the wet-chemically oxidized aluminum effect pigments. Preferably, the elemental aluminum content in the pigments according to the invention is in a range of from 28 to 81 wt.-%, more preferably in a range of from 31 to 77 wt.-%, still more preferably in a range of from 34 to 74 wt.-% and most preferably in a range of from 36 to 71 wt.-%, in each case relative to the total weight of the uncoated, wet-chemically oxidized aluminum effect pigments.

Although wet-chemically oxidized aluminum effect pigments have a very large surface area, to and/or in which large amounts of water are bonded and/or contained, it has been shown, surprisingly, that in relation to the wet-chemically produced aluminum oxide very small amounts of a metal oxide layer which differs from aluminum oxide already effectively reduce or completely suppress an after-oxidation. It has furthermore been shown, surprisingly, that in combination with the organic polymer layer applied according to the invention over, preferably onto, the metal oxide layer which differs from aluminum oxide, a very small amount of the metal oxide layer in relation to the wet-chemically produced aluminum oxide layer is achieved a surprisingly high resistance to, for example, oxidizing conditions. Since a thick metal oxide layer impairs the optical quality of the pigments and in particular reduces the covering power of the pigments, i.e. the area covered per unit weight of pigment, the present invention makes possible the provision of colored aluminum effect pigments of particularly high optical quality with a high stability, in particular of long-lasting color stability.

The ratio of the metal oxide, in particular silicon oxide, which differs from aluminum oxide and is applied in the form of the metal oxide layer, to the aluminum oxide contained in the wet-chemically produced aluminum oxide layer is in a range of from 1:1 to 1:40, preferably in a range of from 1:1.2 to 1:36, more preferably in a range of from 1:1.5 to 1:32 and still more preferably in a range of from 1:1.8 to 1:28. In particular, in others of the abovementioned embodiments it is preferred that the ratio of the metal oxide, in particular silicon oxide, which differs from aluminum oxide and is applied in the form of the metal oxide layer, to the aluminum oxide contained in the wet-chemically produced aluminum oxide layer is in a range of from 1:2 to 1:25, preferably in a range of from 1:2.2 to 1:21, more preferably in a range of from 1:2.4 to 1:18 and still more preferably in a range of from 1:2.5 to 1:15. The abovementioned ratios represent the ratio of the weight of the applied metal oxide which differs from aluminum oxide with respect to the weight of the aluminum oxide produced by wet-chemical oxidation.

The amount of the aluminum oxide contained in the wet-chemically produced aluminum oxide layer can take place, for example, by determination of the amount of elemental aluminum contained in the substrate, determination of the total amount of the aluminum contained in the substrate in the form of aluminum and aluminum oxide, and back-calculation of the $Al_2O_3$ contained in the wet-chemically produced aluminum oxide layer. The determination of the elemental aluminum content can be, for example, gas volumetric. For this, it can be necessary first to partially dissolve the pigments in suitable solvents, for example organic solvents.

The gas volumetric determination of the aluminum contained in the substrate can be carried out, for example, using the following method: 0.3 g of the sample is weighed into a porcelain crucible. 50 ml of 5% sodium hydroxide solution is introduced into a 250-ml conical flask and the porcelain crucible is placed on the NaOH solution such that it floats. The conical flask is then temperature-controlled to 20° C. A gas burette with a compensating vessel is then connected to the conical flask in a gas-tight manner and set to 0. Thereafter, the conical flask is shaken until the crucible tips over and the pigment can react completely with the NaOH solution. The hydrogen that forms displaces the water in the gas burette.

$$p = p_{read} + c - d \text{ (in torr)}$$

$p_{read}$=pressure read off (in torr)
c=correction of the barometer level read off: −2.6 torr (for 760 torr and 20° C.)
d=saturation pressure of water vapor for 5% sodium hydroxide solution: 16.7 torr (760 torr 20° C.)
p=corrected pressure (in torr)

The value p (in torr) obtained is then inserted into the equation below, with the result that the aluminum content in % can be determined.

$$\% \text{ Metal content} = \frac{p[\text{torr}] \& V[\text{ml}]}{\text{Wt.}[\text{mg}]} * \left( \frac{273[K] * 100}{293[K] * 760[\text{torr}]} \right) * \left( \frac{2 * 26.98[\text{mg/mmol}]}{3 * 22.442[\text{ml/mmol}]} \right)$$

V=volume read off in ml
Wt.=amount weighed out in mg
Normal pressure in torr: 760
Normal pressure in pascal: $1013 \cdot 10^2$ Pa
Standard temperature: 0° C.=273 K
Working temperature: 20° C.=293 K To achieve particularly pleasing color shades, it has furthermore proved advantageous for the wet-chemically produced aluminum oxide layer to have a certain minimum thickness. In further embodiments the wet-chemically produced aluminum oxide layer therefore has a thickness of at least 30 nm, preferably of at least 35 nm, more preferably of at least 45 nm, still more preferably of at least 55 nm. The thickness of the wet-chemically produced aluminum oxide layer is determined here as the average value by means of SEM on 20 randomly selected pigments.

However, since the wet-chemically produced aluminum oxide layer is much less ductile compared with the original aluminum, a corresponding pigment has a significantly reduced deformability. In further embodiments it is therefore preferred that the thickness of the wet-chemically produced aluminum oxide layer has at most 300 nm, preferably at most 250 nm, more preferably at most 210 nm and still more preferably at most 160 nm.

In particular, in others of the abovementioned embodiments it is preferred that the thickness of the wet-chemically produced aluminum oxide layer is in a range of from 30 nm to 300 nm, preferably in a range of from 35 nm to 250 nm, more preferably in a range of from 45 nm to 210 nm and still more preferably in a range of from 55 nm to 160 nm. For example, in further particularly preferred embodiments it is preferred that the thickness of the wet-chemically produced aluminum oxide layer is in a range of from 60 to 120 nm.

Figure 2:
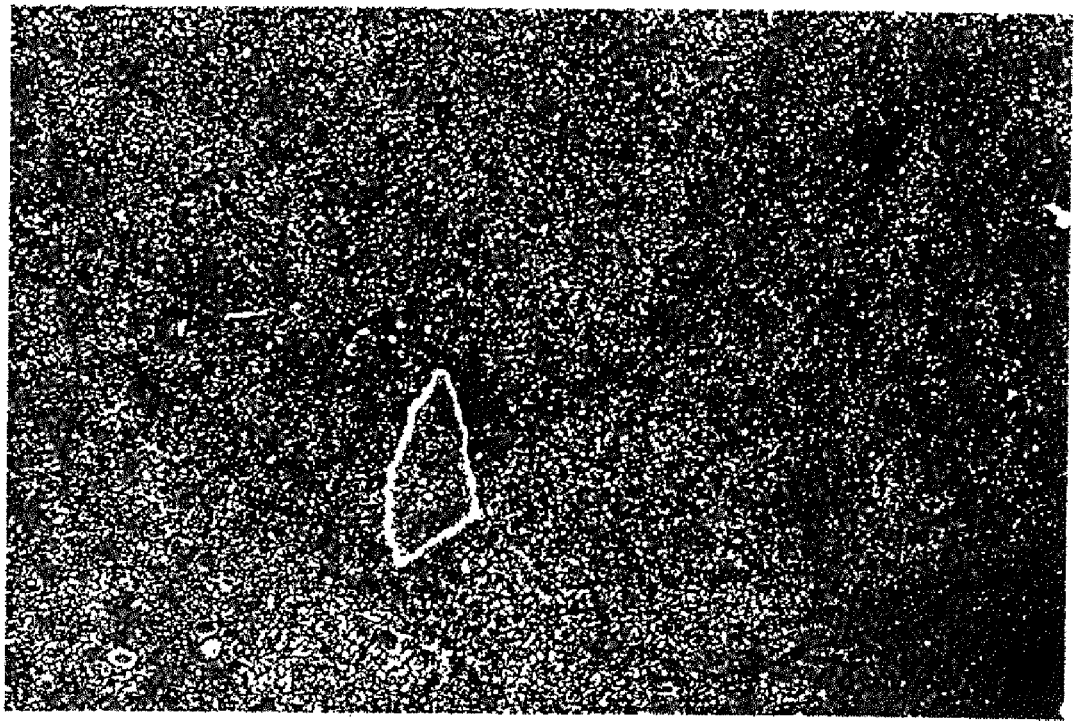
FIG. 2 shows an SEM analysis of the surface of a wet-chemically oxidized aluminum effect pigment of the same type as in FIG. 1 at an identical magnification. The uniformly formed surface structures can be readily seen.
Figure 3:
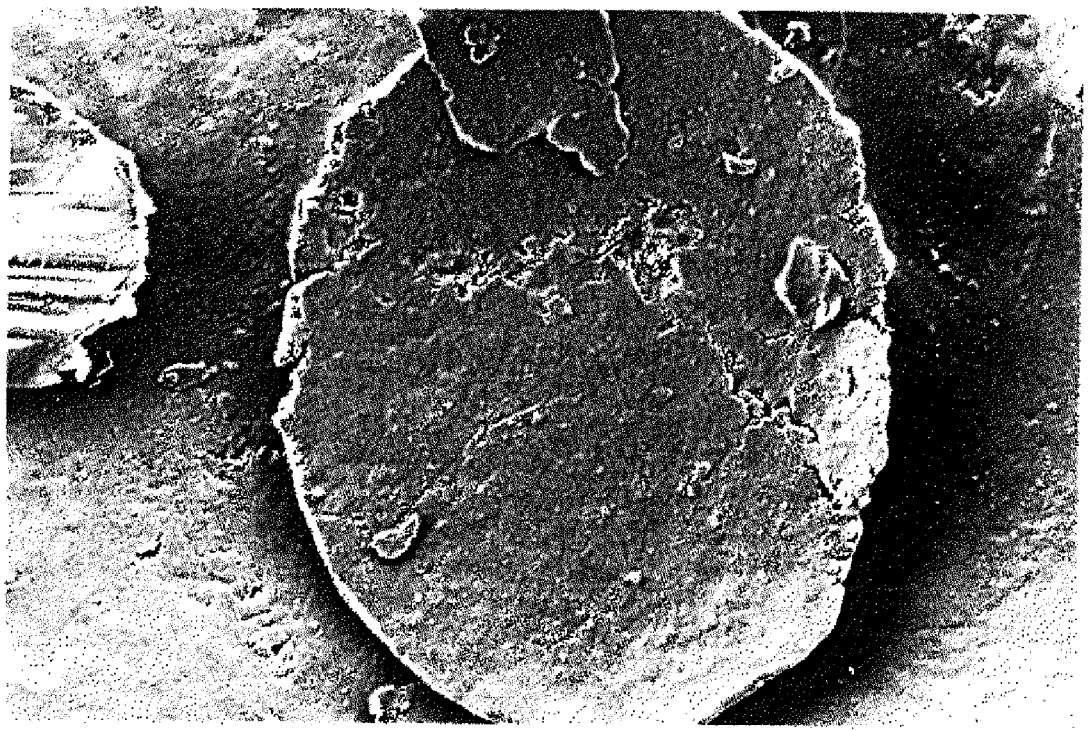
FIG. 3 shows an SEM analysis of further aluminum effect pigments before the wet-chemical oxidation.
Figure 4:
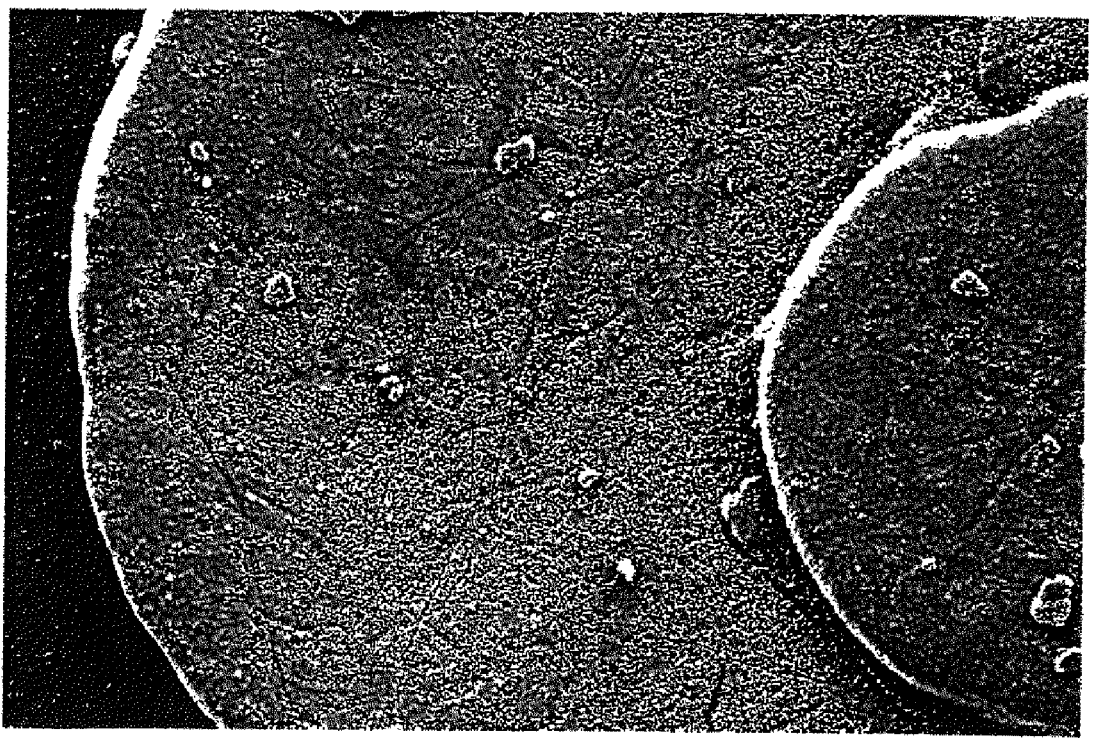
FIG. 4 shows an SEM analysis of an aluminum effect pigment of the type from FIG. 3 after the wet-chemical oxidation at an identical magnification.
Figure 5:
FIG. 5 shows an SEM analysis of further aluminum effect pigments before the wet-chemical oxidation.
Figure 6:
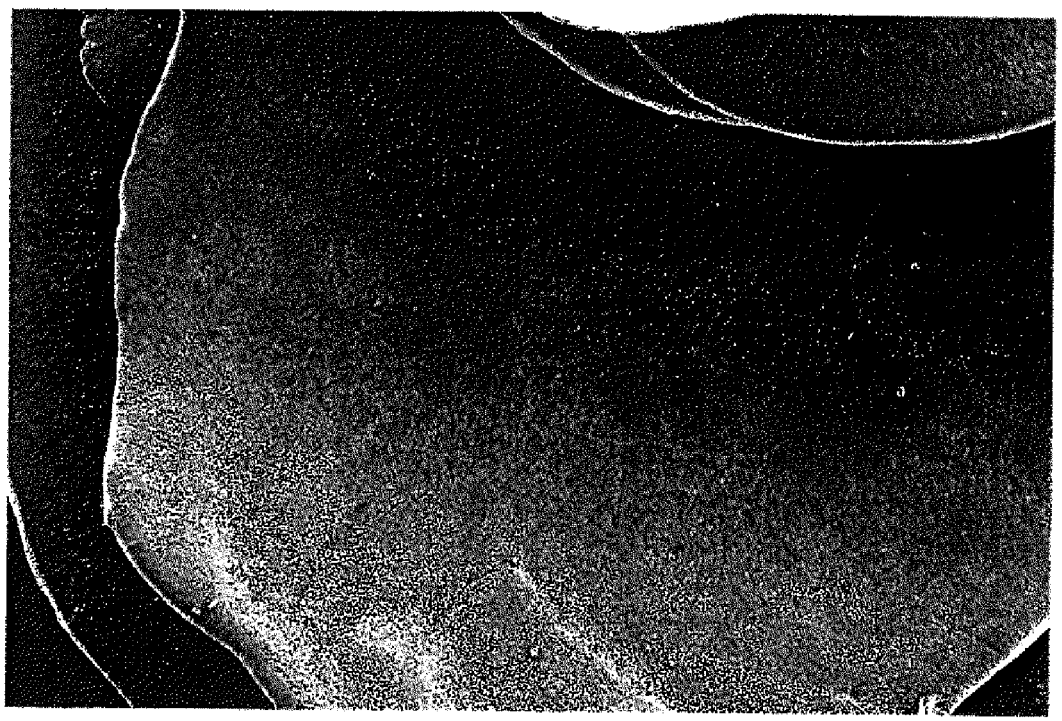
FIG. 6 shows an SEM analysis of an aluminum effect pigment of the type from FIG. 5 after the wet-chemical oxidation at an identical magnification.
Figure 7:
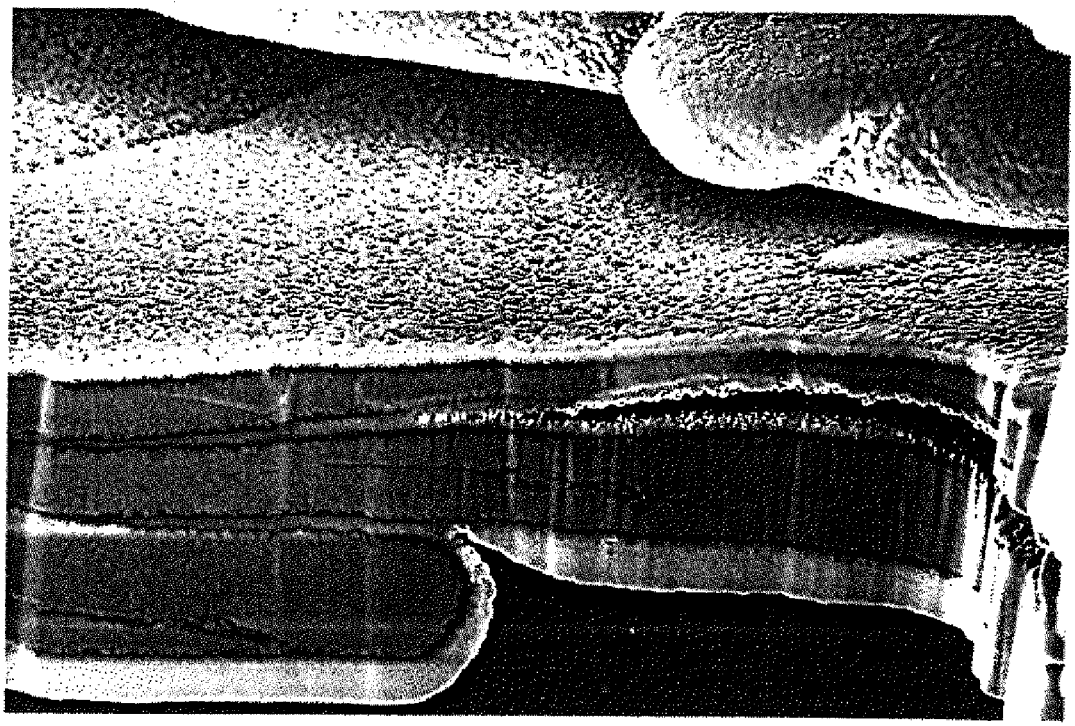
FIGS. 7 and 8 show SEM analyses of polished cross-sections of wet-chemically oxidized aluminum effect pigments. The non-oxidized core of the pigments and the wet-chemically produced, enveloping aluminum oxide layer can be clearly seen.
Figure 8:
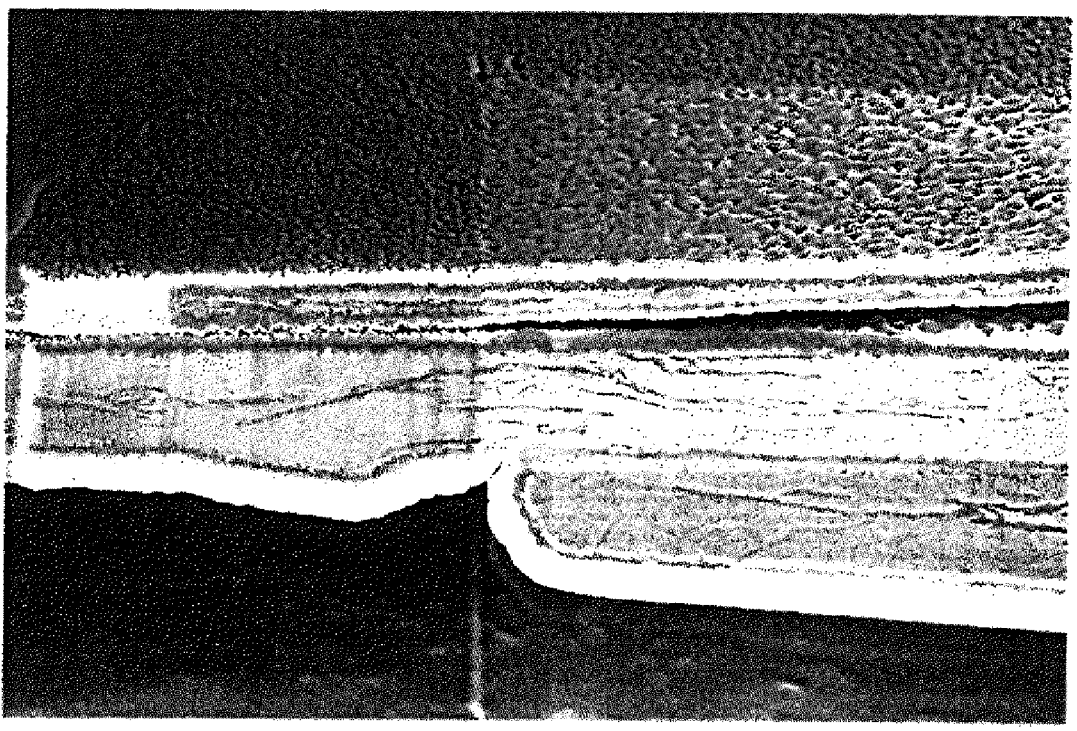
Figure 9:
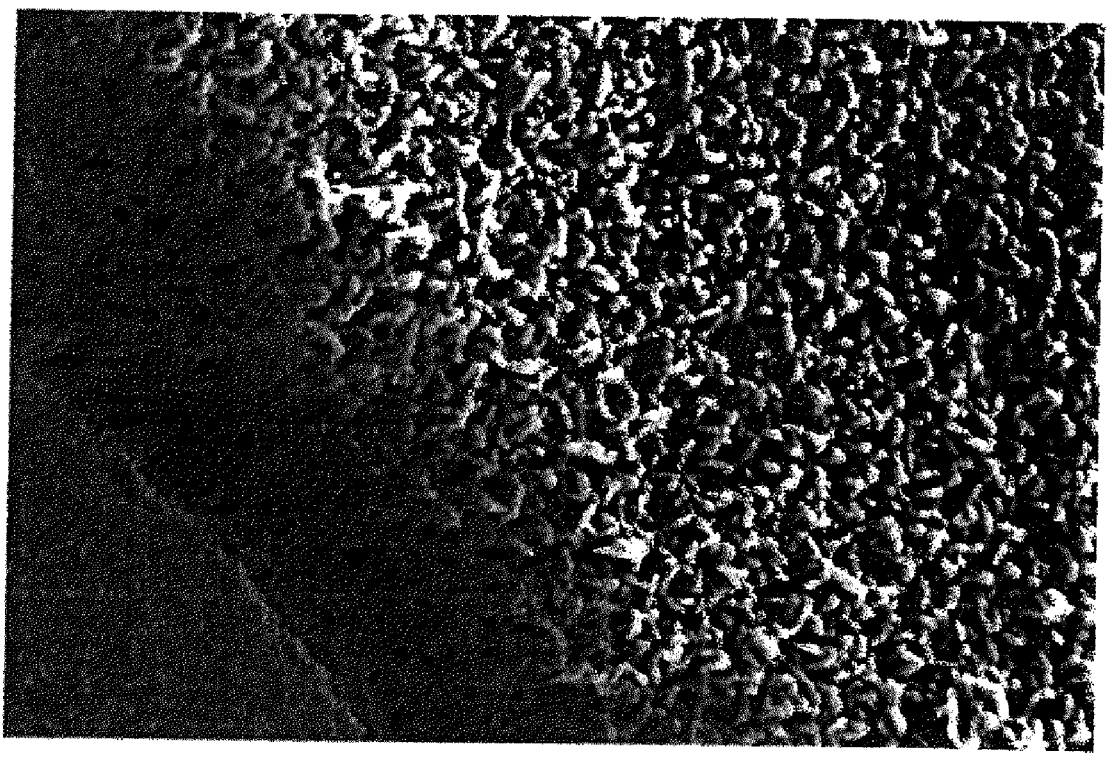
FIG. 9 shows an SEM analysis of a polished cross-section of a wet-chemically oxidized aluminum effect pigment at a 2.5 times higher magnification compared with the magnification of FIG. 7 or 8. The uniformly formed, porous oxide coating formed can be readily seen here.
Figure 10:
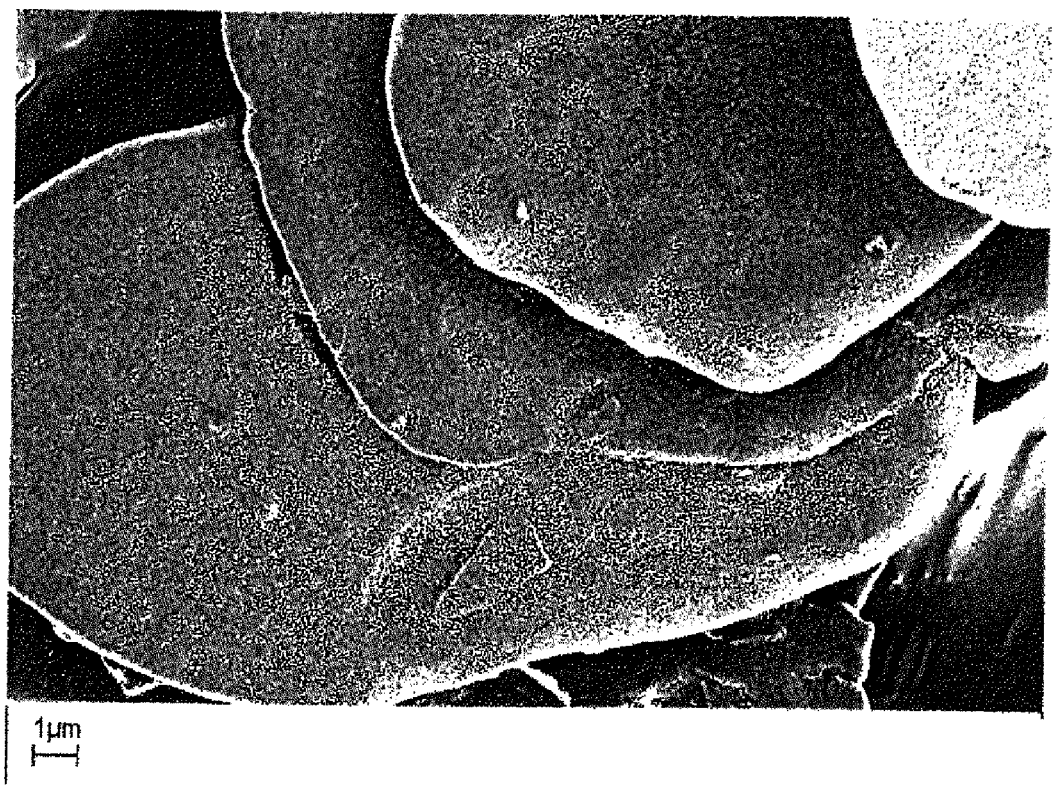
FIGS. 10 and 11 show SEM analyses of uncoated wet-chemically oxidized aluminum pigments as a comparison example.
Figure 11:
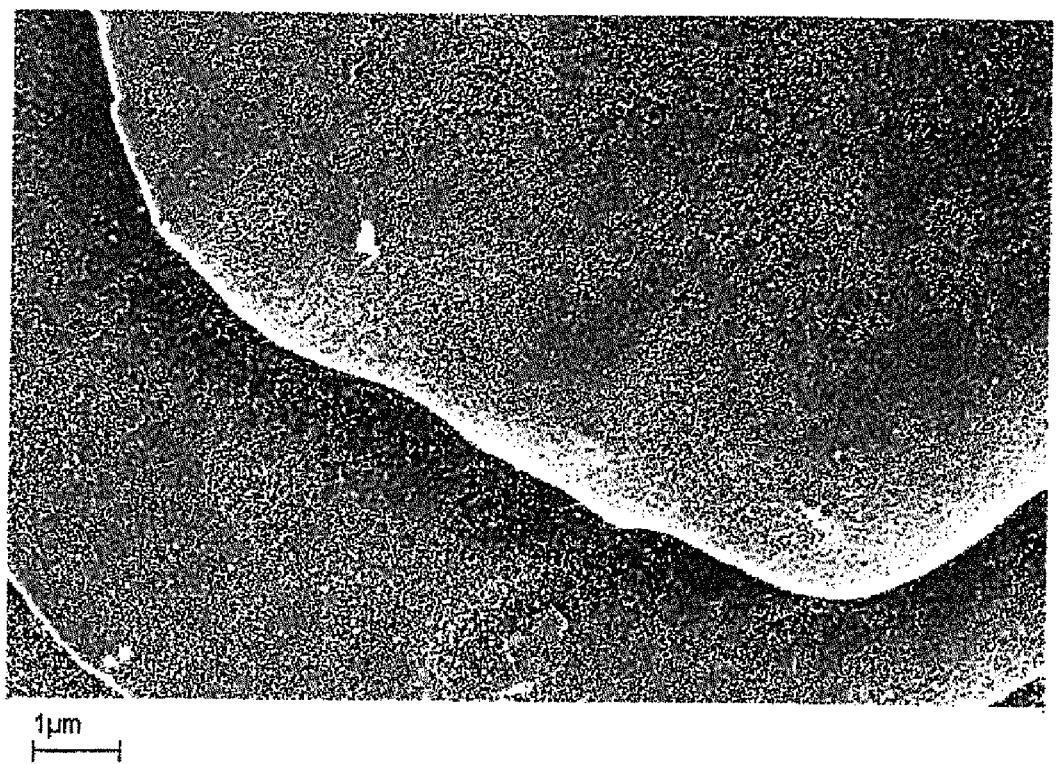
Figure 12:
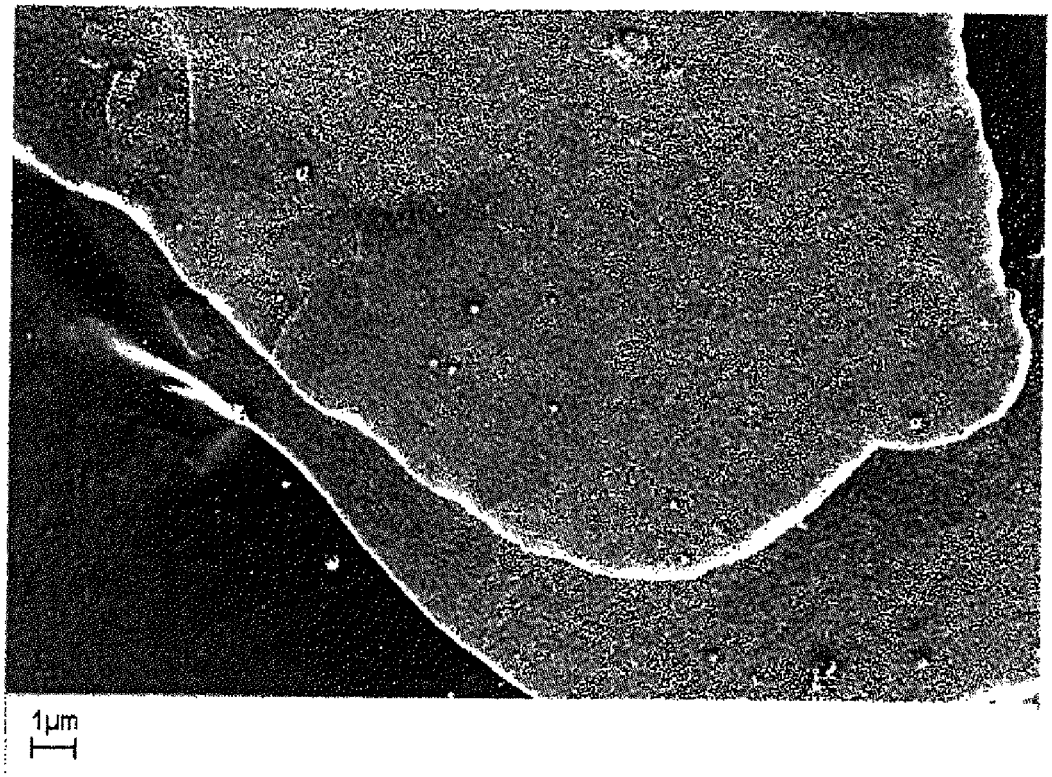
FIGS. 12 and 13 show SEM analyses of wet-chemically oxidized aluminum pigments, as in FIGS. 10 and 11, after the application of a silicon oxide layer.
Figure 13:
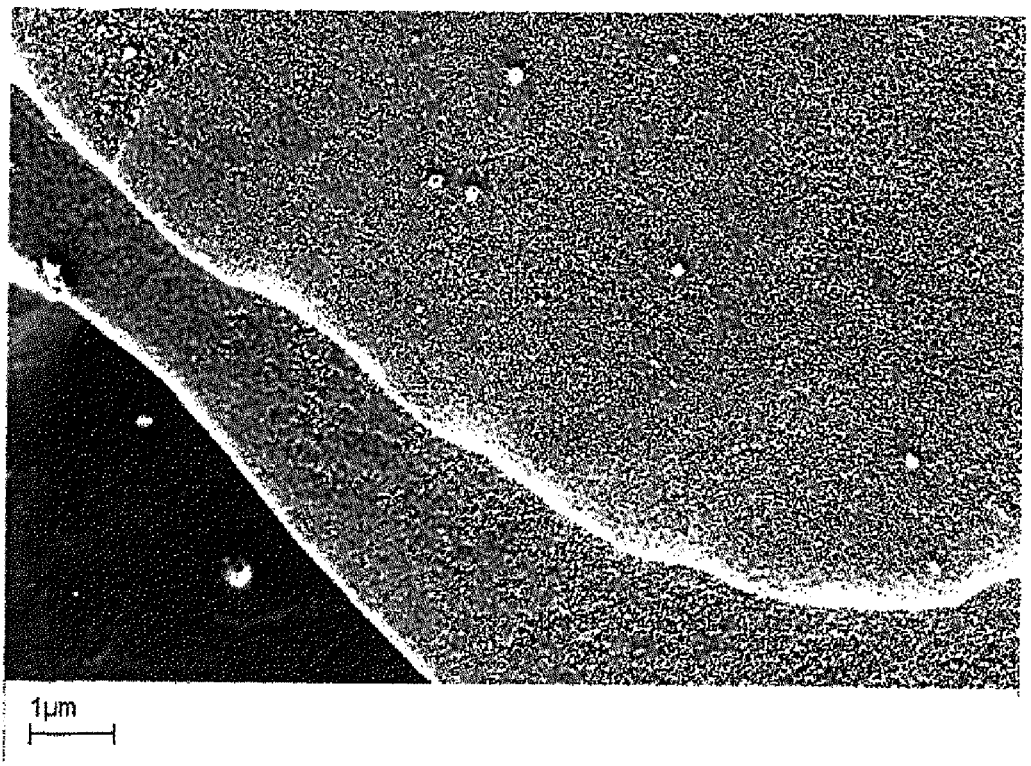
Figure 14:
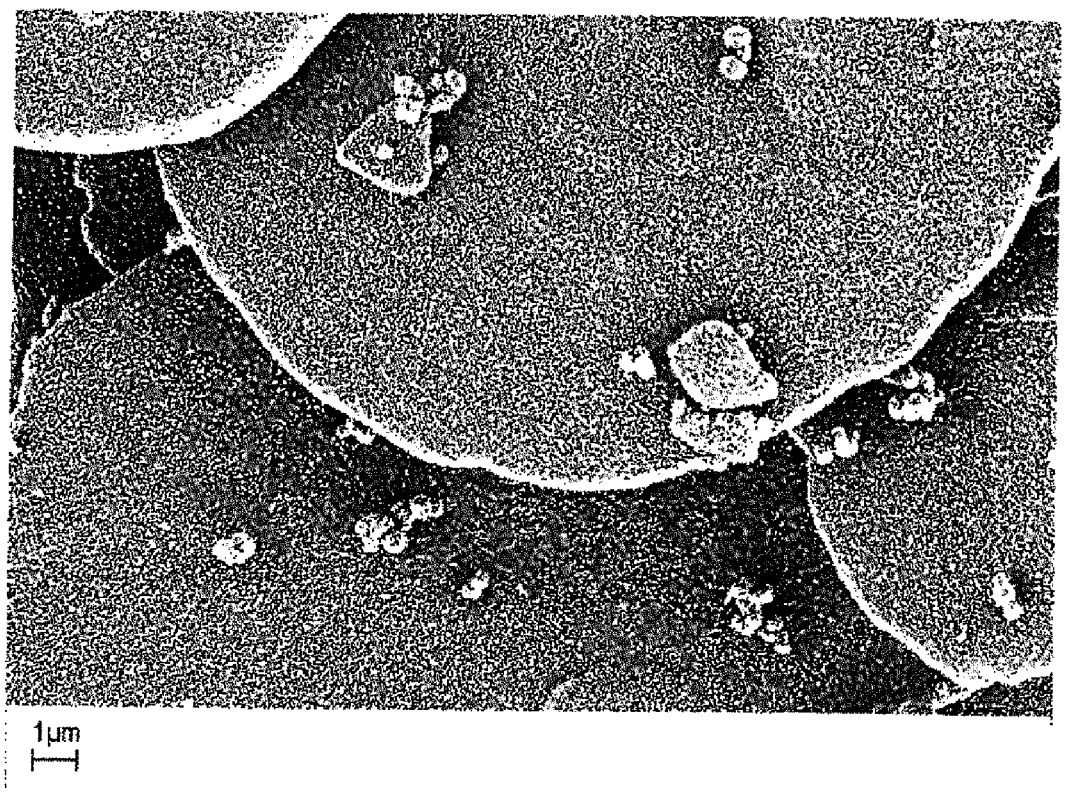
FIGS. 14 and 15 show the SEM analyses of aluminum pigments wet-chemically oxidized and provided with a silicon oxide layer, as shown in FIGS. 12 and 13, in which an organic polymer layer is additionally applied.
Figure 15:
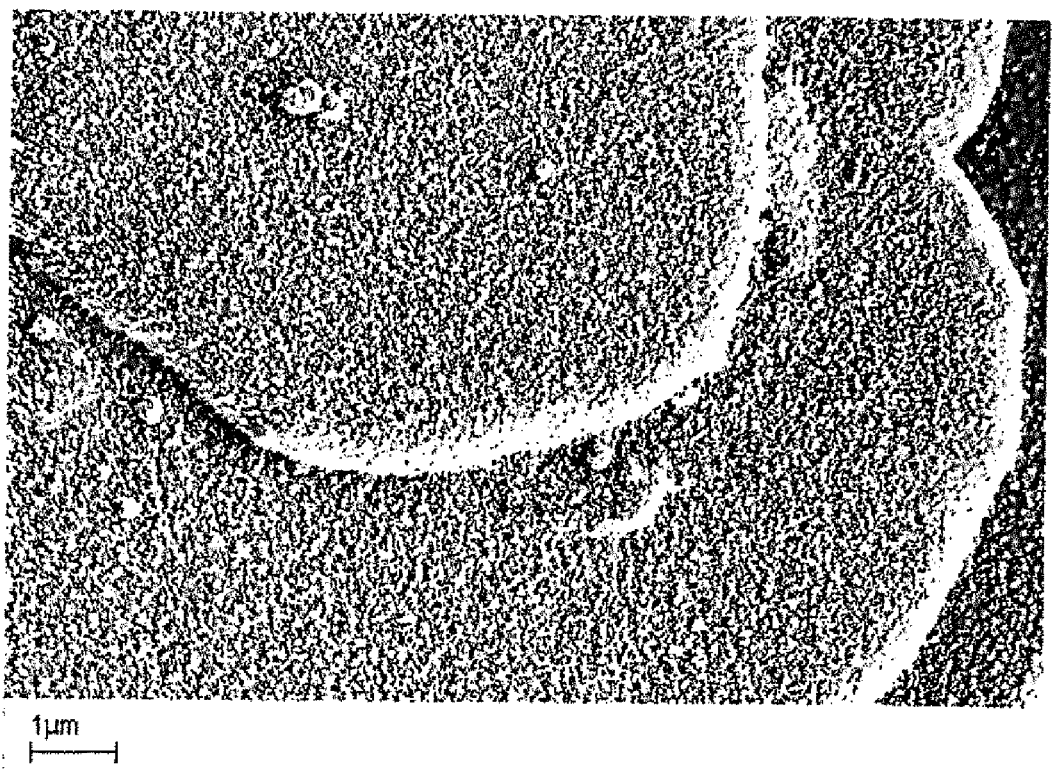

Without being understood as limiting the invention, the inventors believe that the metal oxide layer applied by means of the hydrolysis reaction, preferably the sol-gel process, consumes not only the water bonded in or on the wet-chemically produced aluminum oxide layer. Thus, BET measurements have shown that the BET surface area of a wet-chemically oxidized aluminum effect pigment, as shown in FIG. 2, falls from 35.4 m²/g to 5.2 m²/g due to the application of a silicon oxide coating. Without being understood as limiting the invention, the inventors believe that the metal oxide coating which differs from aluminum oxide and is applied according to the invention fills the hollow spaces between the structures formed by means of the wet-chemical oxidation and therefore drastically reduces the BET surface area. In the case of aluminum effect pigments of similar size without wet-chemical oxidation, on the other hand, it is found that the BET surface area in the case of pigments with a higher $D_{50}$ remains approximately the same (1.4 m$^2$/g before and after the application of a metal oxide coating which differs from aluminum oxide) or in the case of pigments with a lower $D_{50}$ falls only slightly from, for example, 4.2 m$^2$/g to 3.7 m$^2$/g. The slight reduction in the BET surface area of the pigments with a low $D_{50}$ value is attributed to the fact that these pigments have a larger amount of fines and these very small particles are at least partially incorporated into the metal oxide coating. At the same time, however, the BET surface area is not reduced to the original BET size of the pigments before the wet-chemical oxidation (2.6 m$^2$/g), which the corresponding SEM photographs also show.

The surface structures produced by means of wet-chemical oxidation are also still clearly recognizable after the application of the metal oxide layer which differs from aluminum oxide. Since the desired color effect is based on interference effects on the structures produced by means of the wet-chemical oxidation, filling these hollow spaces offers a mechanical stabilizing, which is of particularly high importance for the wet-chemically oxidized aluminum effect pigments used according to the invention. In further embodiments it is therefore preferred that the amount of the at least one metal oxide layer which differs from aluminum oxide and is applied to the surface of the wet-chemically oxidized aluminum effect pigment is at least 0.8 wt.-%, preferably at least 1.2 wt.-%, more preferably at least 1.6 wt.-%, still more preferably at least 1.9 wt.-% and most preferably at least 2.1 wt.-%, in each case relative to the total weight of the uncoated, wet-chemically oxidized aluminum effect pigments. In particular, in further embodiments it is preferred that the BET surface area of the pigments according to the invention after application of the metal oxide layer is at most 30%, preferably at most 25%, more preferably at most 22%, still more preferably at most 19% and most preferably at most 16%, in each case relative to the BET surface area of the wet-chemically oxidized aluminum effect pigments before the application of the metal oxide layer which differs from aluminum oxide. The determination of the BET surface area can be carried out, for example, by means of a BELsorp mini II from the company BEL Inc. based in Japan.

A metal oxide layer which differs from aluminum oxide and is too thick, however, impairs the optical properties and reduces the covering power of the pigments according to the invention. In further embodiments it is therefore preferred that the amount of the at least one metal oxide layer which differs from aluminum oxide is at most 20 wt.-%, preferably at most 17 wt.-%, more preferably at most 16 wt.-%, still more preferably at most 15 wt.-% and most preferably at most 14 wt.-%, in each case relative to the total weight of the uncoated, wet-chemically oxidized aluminum effect pigments. In particular, in further embodiments it is preferred that the amount of the at least one metal oxide layer which differs from aluminum oxide is in a range of from 0.8 wt.-% to 20 wt.-%, preferably from 1.2 wt.-% to 17 wt.-%, more preferably from 1.6 wt.-% to 16 wt.-%, still more preferably from 1.9 wt.-% to 15 wt.-% and most preferably from 2.1 wt.-% to 14 wt.-%, in each case relative to the total weight of the uncoated, wet-chemically oxidized aluminum effect pigments.

The term "wet-chemically produced aluminum oxide layer" in the context of the present invention denotes the oxide layer formed on the aluminum effect pigment surface as a consequence of the wet-chemical oxidation. Water can be bonded in this, as a result of which the layer can partially or completely correspond to the formal composition of aluminum hydroxide (Al(OH)$_3$). In particular, however, it is preferred that the wet-chemically produced aluminum oxide layer consists of Al$_2$O$_3$ to the extent of at least 30 mol.-%, preferably to the extent of at least 40 mol.-%, more preferably to the extent of at least 60 mol.-% and still more preferably to the extent of at least 80 mol.-%, in each case relative to the total molar amount of the aluminum contained in the wet-chemically produced aluminum oxide layer. If aluminum effect pigments which do not consist of pure aluminum, and consequently consist of an aluminum alloy, are used, the correspondingly wet-chemically produced oxide layer can of course also contain other metals and/or metal oxides. In the case of an aluminum alloy also, the above data in mol.-% relate only to the total molar amount of aluminum contained in the wet-chemically produced aluminum alloy oxide layer.

The metal oxide which is to be applied according to the invention to the wet-chemically oxidized aluminum effect pigments is not aluminum oxide. Metal oxides which can be applied according to the invention to the wet-chemically oxidized aluminum effect pigments are, for example, selected from the group consisting of silicon oxide, boron oxide, zirconium oxide, cerium oxide, iron oxide, titanium oxide, chromium oxide, tin oxide, molybdenum oxide, oxide hydrates thereof, hydroxides thereof and mixtures thereof. In particular, in further embodiments it is preferred that the metal oxides which differ from aluminum oxide and are applied as metal oxide layer have no noticeable intrinsic color, such as, for example, silicon oxide, boron oxide, zirconium oxide, titanium oxide, oxide hydrates thereof, hydroxides thereof and mixtures thereof. A metal oxide which is particularly suitable for producing the at least one metal oxide layer which is to be applied according to the invention is silicon oxide. In further, particularly preferred embodiments, the at least one metal oxide layer therefore comprises silicon oxide. According to a further preferred embodiment, the at least one metal oxide layer substantially consists of silicon oxide or still more preferably consists of silicon oxide, hydroxides thereof or mixtures of these. In others of the abovementioned embodiments, the at least one metal oxide layer substantially consists of silicon oxide, preferably SiO$_2$.

In further embodiments it is preferred that the pigments according to the invention have a high refractive index metal chalcogenide layer, preferably a high refractive index metal oxide layer, in addition to the at least one metal oxide layer which differs from aluminum oxide. Iron oxide layers are an example of such high refractive index metal oxide layers.

The term "substantially consists of" in the context of the present invention means that at least 90 wt.-%, more preferably at least 95 wt.-%, still more preferably at least 99 wt.-% and most preferably at least 99.9 wt.-% consists of the substance in question, if this is not defined otherwise in the individual case. Within the framework of this invention, for example, by the term "substantially consisting of silicon oxide" is meant that the layer predominantly consists of silicon oxide, preferably SiO$_2$, but can also contain up to 20 wt.-% water, relative to the silicon oxide layer. Furthermore, the silicon oxide, produced, for example, by means of the sol-gel process from tetraalkoxysilanes, can contain up to 5 wt.-% alkoxy groups which have not been hydrolyzed and condensed. This applies correspondingly to other metal oxides which differ from aluminum oxide and are being or are applied as metal oxide layer.

Preferably, the at least one, preferably one (number: 1), metal oxide layer substantially, preferably completely, consists of silicon oxide, particularly preferably $SiO_2$. In the context of the invention, by one (number: 1) metal oxide layer is also meant a structure of several layers of identical substance, which are applied successively directly on one another in terms of process technology. In further particularly preferred embodiments, the at least one enveloping metal oxide layer is one (number: 1) silicon oxide layer, preferably one (number: 1) $SiO_2$ layer.

The term "metal oxide layer" in the context of the present invention relates to a metal oxide layer which differs from aluminum oxide and is preferably produced by means of a hydrolysis reaction, in particular by means of the sol-gel process, and which is applied to the aluminum oxide layer produced on the aluminum effect pigment by wet-chemical oxidation. A particularly preferred type of metal oxide layer in the context of the present invention comprises or consists of silicon oxide, preferably $SiO_2$. In particular, it is preferred that the abovementioned coating substantially consists of silicon oxide, preferably $SiO_2$. The term "metal oxide layer" in the context of the present invention does not include inorganic/organic mixed layers such as are described in US 2008/0249209 A1.

In particular, in further embodiments it is preferred that the coated pigments according to the invention have one (number: 1) single metal oxide layer according to the invention which differs from aluminum oxide.

The "organic polymer layer" in the context of the present invention is preferably a non-reactive organic polymer layer. A non-reactive organic polymer layer in the context of the present invention is substantially completely, preferably completely, cured. An organic polymer layer cured in such a way consequently, for example, does not substantially react or does not react at all with the binder of a coating agent, such as, for example, a varnish, for example a powder coating, or a paint. According to a preferred variant, no reaction takes place between the cured organic polymer layer and the binder of a coating agent. A large number of polymers known to a person skilled in the art can be used as organic polymers. In particular, the "organic polymer layer" is not a coating of not yet cured binder, such as is disclosed in WO 2005/063897 A2. A binder is characterized in that it cures only later in the use, for example, as a resin/curing agent system or by radical polymerization. Examples of organic polymers which can be used in particular for improving the chemical resistance in the present invention are polyacrylates, polymethacrylates, polyacrylamides, polyacrylonitriles, polyvinyl chlorides, polyvinyl acetates, polyamides, polyalkenes, polydienes, polyalkynes, polyalkylene glycols, epoxy resins, polyesters, polyethers, polyols, polyurethanes, polycarbonates, polyethylene terephthalates, plastics alloys and mixtures thereof. In particular, in further embodiments it is preferred that the organic polymer layer is applied directly to the metal oxide layer which differs from aluminum oxide. Here, it must be understood that a contact can also be present to a limited extent between the wet-chemically produced aluminum oxide layer and the organic polymer layer. According to a preferred variant of the invention, no contact is present between the aluminum oxide layer produced by wet-chemical oxidation the organic polymer layer.

To achieve the desired high stability or resistance, for example vis-à-vis corrosive media, it has proved necessary for a certain minimum amount of the organic polymer layer to be applied, with the result that a substantially complete, preferably complete, enveloping of the metal oxide layer which differs from aluminum oxide is present. In further embodiments it is preferred in particular that the proportion of the at least one organic polymer layer is at least 8 wt.-%, preferably at least 9 wt.-%, more preferably at least 9.5 wt.-%, still more preferably at least 10 wt.-% and most preferably at least 11 wt.-%, in each case relative to the total weight of the uncoated, wet-chemically oxidized aluminum effect pigments.

The application of very thick organic polymer layers, however, has proved to be of little advantage, since only slight further improvements in the chemical resistance are achieved but, for example, additional costs arise and the optical quality of the pigments, in particular the covering power, deteriorates. In further embodiments the amount of the at least one organic polymer layer is therefore at most 40 wt.-%, preferably at most 35 wt.-%, more preferably at most 30 wt.-%, still more preferably at most 23 wt.-% and most preferably at most 18 wt.-%, in each case relative to the total weight of the uncoated, wet-chemically oxidized aluminum effect pigments.

In others of the abovementioned embodiments, the amount of the at least one organic polymer layer is in a range of from 8 to 40 wt.-%, preferably in a range of from 9 to 35 wt.-%, more preferably in a range of from 9.5 to 30 wt.-%, still more preferably in a range of from 10 to 23 wt.-%, and most preferably in a range of from 11 to 18 wt.-%, in each case relative to the total weight of the uncoated, wet-chemically oxidized aluminum effect pigments.

In the case of complex layer structures of organic and/or inorganic layers, sputter techniques in combination with surface-sensitive analytical methods, such as ESCA and/or SIMS, in particular TOF-SIMS, are recommended for analysis of such layers.

It has been found that in further embodiments it is preferred that the pigments according to the invention have an average thickness of the organic polymer layer in a range of from 80 nm to 300 nm, preferably from 100 nm to 250 nm and particularly preferably from 120 nm to 230 nm. The abovementioned average thickness of the organic polymer layer can be determined by SEM as the arithmetic mean of the average thickness of at least 20 randomly selected pigments. It has thus been shown that at an average thickness of the organic polymer layer of less than 80 nm the advantageous properties of the pigments according to the invention are not sufficiently pronounced for certain uses. Furthermore, the loss of covering power and/or gloss in thick organic polymer layers counteracts the object of the present invention of providing aluminum effect pigments having pleasing optical properties, with the result that the thickness of the coating should be chosen as low as possible.

According to further preferred embodiments, the at least one organic polymer layer substantially consists of a polymer which is selected from the group consisting of polyacrylate, polymethacrylate, polyacrylamide, polyacrylonitrile, polyvinyl chloride, polyvinyl acetate, polyamide, polyalkene, polydiene, polyalkyne, polyalkylene glycol, epoxy resin, polyester, polyether, polyol, polyurethane, polycarbonate, polyethylene terephthalate, polymer alloys and mixtures thereof.

In a variant of the invention, it is preferred that the organic polymer layer comprises at most 10 wt.-%, preferably at most 5 wt.-%, more preferably at most 1 wt.-% and still more preferably at most 0.1 wt.-% fluoropolymers, in each case relative to the total weight of the polymer layer. In particular, it is preferred that no fluoropolymers are contained in the organic polymer layer.

According to others of the abovementioned embodiments, the at least one organic polymer layer substantially consists of a polymer which is selected from the group consisting of polyacrylate, polymethacrylate, polyurethane, polyester and mixtures thereof. Pigments according to the invention having at least one such organic polymer layer are characterized, for example, by an increased UV resistance. An increased UV stability is desired when the aluminum effect pigments according to the invention are used in external applications, such as, for example, in an automobile varnish, a façade paint, etc. For example, polyacrylates, polymethacrylates or mixtures thereof have proved to be particularly suitable polymers for the production of organic polymer layers with increased UV resistance. In further embodiments of the invention, the at least one organic polymer layer therefore substantially consists of polyacrylates, polymethacrylates or mixtures thereof.

The following are used, for example, as monomers for the production of polyacrylates and polymethacrylates: isoamyl acrylate, lauryl acrylate, stearyl acrylate, butoxyethyl acrylate, ethoxy-diethylene glycol acrylate, methoxytriethylene glycol acrylate, methoxy-polyethylene glycol acrylate, methoxy-dipropylene glycol acrylate, phenoxyethyl acrylate, phenoxy-polyethylene glycol acrylate, tetrahydrofurfuryl acrylate, isobornyl acrylates, 2-hydroxyethyl acrylate, 2-hydroxypropyl acrylate, 2-hydroxy-3-phenoxypropyl acrylate, 2-acryloyloxyethylsuccinic acid, 2-acryloyloxyethylphthalic acid, 2-acryloyloxyethyl-2-hydroxyethylphthalic acid, triethylene glycol diacrylate, neopentyl glycol diacrylate, 1,6-hexanediol diacrylate, 1,9-nonanediol diacrylate, dimethyloltricyclodecane diacrylate, trimethylolpropane triacrylate, pentaerythritol triacrylate, pentaerythritol tetraacrylate, dipentaerythritol hexaacrylate, 2-hydroxy-3-acryloyloxypropyl methacrylate, isooctyl acrylate, isomyristyl acrylate, isostearyl acrylate, 2-ethylhexyl diglycol acrylate, 2-hydroxybutyl acrylate, 2-acryloyloxyethylhexahydrophthalic acid, hydroxypivalic acid, neopentyl glycol diacrylate, polytetraethylene glycol diacrylate, ditrimethylolpropane tetraacrylate, methyl methacrylate, ethyl methacrylate, n-butyl methacrylate, isobutyl methacrylate, 2-ethylhexyl methacrylate, isodecyl methacrylate, n-lauryl methacrylate, tridecyl methacrylate, n-stearyl methacrylate, methoxydiethylene glycol methacrylate, methoxypolyethylene glycol methacrylate, cyclohexyl methacrylate, tetrahydrofurfural methacrylate, benzyl methacrylate, phenoxyethyl methacrylate, isobornyl methacrylate, 2-hydroxyethyl methacrylate, 2-hydroxypropyl methacrylate, 2-hydroxybutyl methacrylate, 2-methacryloyloxyethylsuccinic acid, 2-methacroyloxyethylhexahydrophthalic acid, 2-meth acryloyloxyethyl 2-hydroxypropyl phthalate, ethylene glycol dimethacrylate, diethylene glycol dimethacrylate, 1,4-butanediol dimethacrylate, 1,3-butanediol dimethacrylate, 1,6-hexanediol dimethacrylate, 1,9-nonanediol dimethacrylate, trimethylolpropane trimethacrylate, glycerol dimethacrylate, 2-hydroxy-3-acryloyloxypropyl methacrylate, t-butyl methacrylate, isostearyl methacrylate, methoxytriethylene glycol methacrylate, n-butoxyethyl methacrylate, 3-chloro-2-hydroxypropyl methacrylate, triethylene glycol dimethacrylate, neopentyl glycol dimethacrylate or mixtures of these.

Particularly preferably, at least one monomer having at least two, particularly preferably three, reactive double bonds (crosslinking agent) is used. Particularly preferably, the monomer therefore contains or consists of 1,6-hexanediol diacrylate, 1,9-nonanediol diacrylate, dimethyloltricyclodecane diacrylate, neopentyl glycol dimethacrylate, trimethylolpropane triacrylate, trimethylolpropane trimethacrylate or mixtures thereof.

The (meth)acrylate-containing organic polymer layer can furthermore additionally feature acrylic acid, methacrylic acid or mixtures thereof and further radically polymerizable unsaturated compounds.

Furthermore, the (meth)acrylate-containing organic polymer layer can contain (meth)acrylate-containing silanes. The proportion of (meth)acrylate-containing silanes used corresponds here at most to the proportion of other (meth)acrylate monomers used. Preferably, the molar ratio of (meth)acrylate-containing silanes to further (meth)acrylate monomers is 1:2 to 1:40, preferably 1:3 to 1:30.

According to a further variant according to the invention, the organic polymer layer is selected from the group consisting of polyamide, polycarbonate, polyvinyl chloride, polyethylene terephthalate and mixtures thereof. Pigments according to the invention having at least one such organic polymer layer are characterized, for example, by an increased temperature resistance.

According to a preferred embodiment of the invention, the polymer used for the at least one organic polymer layer is temperature-resistant up to a temperature of at least 180° C., further preferably up to a temperature of at least 260° C., still further preferably up to a temperature of at least 350° C. By temperature-resistant is meant that the organic polymer layer of the pigments according to the invention does not melt and/or decompose at the abovementioned temperature. Testing for a possible melting and/or decomposition at a predetermined temperature can be carried out, for example, by means of dynamic differential calorimetry.

According to a further preferred embodiment, physically bonded surface-modifying agents are applied to the organic polymer layer.

It has also been shown that in further embodiments it is advantageous to apply a combination of at least one thin metal oxide layer and at least one thicker organic polymer layer to the wet-chemically oxidized aluminum effect pigments. By means of the combination of a thin metal oxide layer and a thicker organic polymer layer it is possible to achieve an optimum of optical quality and at the same time to achieve an excellent resistance to chemicals and resistance to oxidation. Such pigments are particularly suitable, for example, for stoving processes under particularly demanding conditions in the case of powder coating or coil coating varnishing.

In particular, in further embodiments it is preferred that the coated pigments according to the invention have one (number: 1) metal oxide layer and only one (number: 1) organic polymer layer.

In further embodiments, it is preferred that the at least one organic polymer layer is produced by means of an initiator-induced radical polymerization. It has been found that a rough organic polymer layer can be obtained, for example, in a simple manner by means of this method. Pigments according to the invention having such a surface structure are characterized in that they can be electrostatically charged more easily, as a result of which a simplified application of the pigments according to the invention by means of powder coating is made possible.

In other embodiments, on the other hand, it is preferred that the organic polymer layer is produced by means of thermal polymerization. It is consequently particularly easy, for example, to produce smooth surfaces of the organic polymer layer, which can be embedded better into a varnish, such as, for example, a powder coating or a coil coating varnish, because of a lower binder requirement.

The layer thicknesses of the metal oxide layers and of the organic polymer layers on the pigments according to the invention are determined, for example, by means of SEM photographs on suitable polished cross-sections. For this, the pigments are applied in a varnish and this is cured. The best possible plane-parallel orientation of the platelets in the application medium is to be ensured here. For this, the pigments can be pretreated by suitable additives beforehand. The cured varnish is then polished and the polished cross-section is observed in SEM after conventional sample preparation. Only particles which have a good orientation are selected for the determination. Poorly orientated platelets result in a high error in this method because of the unknown observation angle. The coatings have a very good contrast to the metal core. If the layer thicknesses of the metal oxide layer and of the organic polymer layer cannot be differentiated well, locally resolved EDX analyses can be used before the layer thicknesses are measured. The term "average layer thickness" in the context of the invention denotes the arithmetic mean of the layer thicknesses of the layers of at least 20 pigments. If the coating is non-uniform, the arithmetic mean of the thinnest and the thickest point of the coating of the respective particle is taken. Individual serious deviations which relate, for example, to the inclusion of already coated fine-particled pigments in the coating are not taken into account in the calculation of the average layer thickness.

The metal oxide content can take place via an elemental analysis. Thus, for example, in the case of an $SiO_2$ layer the Si content can be determined and extrapolated to $SiO_2$.

Particularly advantageous combinations of properties of the pigments according to the invention which make possible a broad spectrum of use with excellent optical qualities can be achieved by matching the amount of the at least one metal oxide layer which differs from aluminum oxide to the at least one organic polymer layer. In further embodiments it is preferred, for example, that the sum of the at least one metal oxide layer which differs from aluminum oxide and the at least one organic polymer layer is in the range of from 10 to 50 wt.-%, preferably in the range of from 13 to 40 wt.-%, more preferably in the range of from 14 to 35 wt.-%, still more preferably in the range of from 15 to 33 wt.-% and most preferably in the range of from 16 to 29 wt.-%, in each case relative to the total weight of the uncoated, wet-chemically oxidized aluminum effect pigments.

It has furthermore been shown that for many uses it is advantageous to apply more organic polymer material than metal oxide which differs from aluminum oxide. In particular, in further embodiments it is advantageous for the weight ratio of the at least one metal oxide layer which differs from aluminum oxide to the at least one organic polymer layer on in a range of from 1:2 to 1:20, preferably in a range of from 1:2.2 to 1:17, further preferably in a range of from 1:2.5 to 1:15 and still further preferably in a range of from 1:2.7 to 1:13 and most preferably in a range of from 1:3 to 1:10, wherein the percentages by weight forming the basis in each case are relative to the total weight of the uncoated, wet-chemically oxidized aluminum effect pigments.

In particular, in others of the abovementioned embodiments it is advantageous for the sum of the at least one metal oxide layer which differs from aluminum oxide and the at least one organic polymer layer to have in the range of from 10 to 50 wt.-% and for the weight ratio of the at least one metal oxide layer which differs from aluminum oxide to the at least one organic polymer layer to have in a range of from 1:2 to 1:20. Preferably, in others of the abovementioned embodiments the sum of the at least one metal oxide layer which differs from aluminum oxide and the at least one organic polymer layer is in the range of from 13 to 40 wt.-% and the weight ratio of the at least one metal oxide layer which differs from aluminum oxide to the at least one organic polymer layer is in a range of from 1:2.2 to 1:17. In further, more preferred embodiments the sum of the at least one metal oxide layer which differs from aluminum oxide and the at least one organic polymer layer is in the range of from 14 to 35 wt.-% and the weight ratio of the at least one metal oxide layer which differs from aluminum oxide to the at least one organic polymer layer is in a range of from 1:2.5 to 1:15. In further, still more preferred embodiments the sum of the at least one metal oxide layer which differs from aluminum oxide and the at least one organic polymer layer is in the range of from 15 to 33 wt.-% and the weight ratio of the at least one metal oxide layer which differs from aluminum oxide to the at least one organic polymer layer is in a range of from 1:2.7 to 1:13.

The abovementioned weight ratios and the wt.-% relate to the weight of the respective coatings, relative to the total weight of the uncoated, wet-chemically oxidized aluminum effect pigments.

One or more further coatings can be applied between the at least one metal oxide layer which differs from aluminum oxide and the at least one organic polymer layer or. Furthermore, one or more further coatings, preferably enveloping coatings, can also be applied to the organic polymer layer. One or more further coatings can of course also be applied between the at least one metal oxide layer which differs from aluminum oxide and the at least one organic polymer layer or can, and one or more further coatings can also be applied, preferably enveloping, to the organic polymer layer.

Thus, the at least one organic polymer layer can be enveloped, for example, by a further metal oxide layer. In particular, in further embodiments it is preferred, however, that additionally at least one layer of an adhesion promoter and/or of another layer component is present between the at least one metal oxide layer which differs from aluminum oxide and the at least one organic polymer layer. The abovementioned intermediate layers can have been produced, for example, from organofunctional silanes, titanates, aluminates, phosphonic acids (e.g. VPA: vinylphosphonic acid), phosphoric acid esters, zirconates and mixtures thereof. Such coatings can consequently bind, for example on the basis of known hydrolysis and condensation reactions, particularly well to the metal surface or the metal oxide surface and at the same time bind via a polymerizable group, such as, for example, a polymerizable double bond, preferably at least one acrylate and/or methacrylate group, to the organic polymer layer. It is important here to match the polymerizable group to the organic polymer in order to make possible an optimum binding. Thus, it is advantageous, for example, to select such an intermediate coating such that it provides radically polymerizable groups if the organic polymer layer is produced by means of radical polymerization.

Particularly preferred adhesion promoters and/or additional layer components are organofunctional silanes. For example, acrylate- and/or methacrylate-containing silanes can be used, in particular (methacryloxymethyl)methyldimethoxysilane, methacryloxymethyltrimethoxysilane, (methacryloxymethyl)methyldiethoxysilane, methacryloxymethyltriethoxysilane, 2-acryloxyethylmethyldimethoxysilane, 2-methacryloxyethyltrimethoxysilane, 3-acryloxypropylmethyldimethoxysilane, 2-acryloxyethyltrimethoxysilane, 2-methacryloxyethyltriethoxysilane, 3-acryloxypropyltrimethoxysilane, 3-acryloxypropyltripropoxysilane, 3-rnethacryloxypropyltriethoxysilane, 3-methacryloxypropyltrimethoxysilane, 3-methacryloxypropyltriacetoxysilane, 3-methacryloxypropylmethyldimethoxysilane, vinyltrichlorosilane, vinyltrimethoxysilane vinyldimethoxymethylsilane, vinyltriethoxysilane, vinyltris(2-methoxyethoxy)silane, vinyltriacetoxysilane or mixtures thereof.

In particular embodiments of the present invention, the abovementioned intermediate layer is not a separate adhesion-promoting coating but is at least partially also polymerized into the layer of plastic, as described in WO 2008/095697 A1, which is hereby incorporated by reference.

In addition, a high refractive index metal chalcogenide layer can be applied to the at least one metal oxide layer and/or the at least one organic polymer layer, in order, for example, to bring about a specific color shade having a soft color flop. The term "high refractive index" in the context of the present invention describes a refractive index of at least 1.95, preferably of at least 2.1 and more preferably of at least 2.2. In particular, in further embodiments it is preferred that the high refractive index metal chalcogenide layer is applied to the at least one metal oxide layer according to the invention.

High refractive index metal chalcogenides in the context of the present invention are preferably selected from the group consisting of metal oxides, metal sulfides, metal selenides, metal tellurides and mixtures thereof. In particular, in further embodiments it is preferred that the high refractive index metal chalcogenide is a high refractive index metal oxide.

In further embodiments it is preferred in particular that the high refractive index metal chalcogenides are colored, high refractive index metal chalcogenides. Examples of colored, high refractive index metal chalcogenides are iron oxides, iron oxide hydrates, vanadium oxides, tungsten oxides, chromium oxides, molybdenum sulfide and mixtures thereof. In further embodiments it is preferred in particular that the high refractive index metal chalcogenide is iron oxide, in particular selected from the group consisting of hematite, goethite, magnetite or mixtures thereof. For example, for provision of pigments for use in the gold-red range, red iron oxide layers which substantially consist of the hematite modification are preferred in particular. For provision of green pigments, in further embodiments it is preferred, on the other hand, to apply chromium(III) hydroxide as the high refractive index metal chalcogenide.

In other embodiments in which, for example, the generation of particular interference effects is to the fore, it is preferred, on the other hand, that the high refractive index metal chalcogenide is combined with a low refractive index metal chalcogenide. In further embodiments the low refractive index metal chalcogenide here preferably has no color, since it serves merely to generate an interference effect. Examples of such colorless, high refractive index metal chalcogenides are titanium oxide, zirconium oxide, zinc oxide, tin oxide, cerium oxide and mixtures thereof.

In others of the abovementioned embodiments, the pigment according to the invention comprises at least one high refractive index metal chalcogenide layer and at least one low refractive index metal chalcogenide layer. The term "low refractive index" in the context of the present invention describes a refractive index of at most 1.8, preferably at most 1.7, more preferably at most 1.65 and still more preferably at most 1.6. It is preferred in particular that the coating is not too thick, in order that an adequate covering power can be achieved. In further embodiments, it is therefore preferred that the pigment according to the invention comprises at most 4 layer packages, more preferably at most 3 layer packages, still more preferably at most 2 layer packages and most preferably at most one layer package comprising a layer of at least one high refractive index metal chalcogenide and a layer of at least one low refractive index metal chalcogenide. In particular, in further embodiments it is preferred that the abovementioned layer packages consist of at least one layer of a colored, high refractive index metal chalcogenide and at least one layer of a colorless, low refractive index metal chalcogenide. The terms "colorless" and "colored" relate to the macroscopic appearance of the respective substances, wherein a whitish, greyish or blackish clouding or a white, grey or black appearance at higher layer thicknesses is not understood as meaning color in the context of the invention.

For the wet-chemical oxidation, the aluminum particles ground, for example, in a ball mill are used without intermediate insertion of a degreasing step. A specific embodiment of such a method is described, for example, in U.S. Pat. No. 5,964,936 A. The wet-chemical oxidation of the aluminum effect pigments is carried out in a mixture with or of at least one water-miscible solvent, water and optionally an acid or base. If an acid is used, the pH of the reaction mixture is preferably set to between 3 and 7. If a base is used, the pH of the reaction mixture is preferably set to between 7 and 12. The determination of the pH is carried out here, for example, with a pH meter of the sympHony type from VWR. The water content, relative to the total amount of the at least one water-miscible solvent and the water, here is up to 63 wt.-%, preferably up to 59 wt.-%, more preferably up to 55 wt.-%. In particular, in further embodiments it is preferred that the abovementioned water content is in a range of from 3 to 42 wt.-%, preferably in a range of from 6 to 33 wt.-%, more preferably in a range of from 8 to 31 wt.-%.

The total amount of water is chosen here such that the amount of water is in a range of from 10 to 150 wt.-%, relative to the weight of the aluminum particles used. In particular, in further embodiments it is preferred that the abovementioned total amount of water is in a range of from 13 to 130 wt.-%, preferably in a range of from 16 to 115 wt.-%, more preferably in a range of from 18 to 95 wt.-% and most preferably in a range of from 20 to 80 wt.-%, in each case relative to the weight of the aluminum effect pigments used.

The term "water-miscible solvent" in the context of the present invention relates to solvents which do not form multiphase systems under standard conditions (25° C., 1013.25 hPa) in the reaction conditions of the decreasing amount of water which are planned for the reaction. Examples are alcohols, such as ethanol, n-propanol, i-propanol, n-butanol, i-butanol, methoxypropanol, glycols, acetone or butyl glycol. It goes without saying that any water contained in the solvent must be calculated into the abovementioned amount of water used in the wet-chemical oxidation. The determination of the amount of water contained in the solvent can be carried out, for example, by means of Karl Fischer titration.

The base for the abovementioned use in the wet-chemical oxidation is preferably selected from the group consisting of aliphatic or aromatic amines, methanolamines, ethanolamines and inorganic bases, e.g. triethylamine, n-butylamine, i-butylamine, dimethanolamine, diethylamine, pyridine, ethylenediamine, diethanolamine, triethanolamine, diisopropylethylamine, ammonia, hydrazine, sodium hydroxide, potassium hydroxide, ammonium hydroxide, ammonium carbonate, ammonium bicarbonate, sodium carbonate, sodium bicarbonate, potassium carbonate, potassium bicarbonate and/or sodium acetate.

The acid for the abovementioned use in the wet-chemical oxidation is preferably selected from the group consisting of phosphoric acid, phosphonic acid, sulfuric acid, hydrochloric acid, acetic acid and nitric acid. The term "phosphoric acid" in the context of the present invention in addition also includes phosphoric acid half-esters.

The reaction temperature of the wet-chemical oxidation is preferably in a range of between 5° C. and 120° C. It must be understood that a person skilled in the art of course adjusts the respective upper limit if the reaction mixture already boils at a lower temperature. In particular, in further embodiments it is preferred that the reaction temperature is between 50 and 95° C.

In the wet-chemical oxidation it is possible to use a large number of aluminum effect pigments which are already known, the aluminum content of which is at least 50 wt.-%, preferably at least 60 wt.-% and more preferably at least 70 wt.-% and still more preferably at least 80 wt.-%. In further embodiments it is preferred that the aluminum content of the aluminum effect pigments is at least 99 wt.-% and in particular preferably at least 99.9 wt.-%. It must be understood that trace constituents of impurities which may be present are not calculated into the abovementioned wt.-%. The term "trace constituents" in the context of the present invention denotes constituents of which the amount is less than 0.01 wt.-%. In further embodiments the aluminum content in the aluminum effect pigments is at least 95 wt.-%, since these have a color scale from pale gold to bronze, largely to completely independently of the alloyed metals. However, in further embodiments it can also be preferred to provide a broader color spectrum, such as, for example, yellow-, green-, red- and red brown-tinged gold shades up to dark brown and black. In this connection, for example, iron, manganese, copper, vanadium, chromium, nickel, cobalt, silicon, magnesium, zinc or titanium have proved to be useful alloy constituents.

The light incident on the platelet-shaped surface of metal effect pigments is reflected as if directed at a mirror. Platelet-shaped metal pigments are therefore particularly suitable for achieving a high gloss in the case of the objects coated with the aluminum effect pigments according to the invention. The platelet-shaped pigments according to the invention are thus aluminum effect pigments.

The aluminum effect pigments according to the invention have an average pigment diameter ($D_{50}$) from a range of from about 1 μm to about 180 μm, preferably from about 3 μm to about 160 μm, still further preferably from about 4 μm to about 120 μm. Pigment diameters from a range of from about 5 μm to about 90 μm, preferably from about 6 μm to about 80 μm, have also proved to be very suitable. The term "$D_{50}$" in the context of the present invention denotes the particle size at which 50% of the abovementioned particle size distribution volume-averaged by means of laser granulometry lies below the value stated. The measurements can be carried out, for example, with the HELOS particle size analyzer from Sympatec GmbH, Clausthal-Zellerfeld, Germany. The dispersing of a dry powder can be carried out here using a dispersing unit of the Rodos T4.1 type under a primary pressure of, for example, 4 bar. Alternatively, the size distribution curve of the particles can be measured, for example, with an apparatus from Quantachrome (apparatus: Cilas 1064) according to the manufacturer's instructions. For this, 1.5 g of the powdered coating material is dispersed in approx. 100 ml isopropanol, treated for 300 seconds in an ultrasound bath (apparatus: Sanorex IK 52, Bandelin) and then introduced by means of a Pasteur pipette into the sample preparation cell of the measuring apparatus and measured several times. The resulting average values are obtained from the individual measurement results. The scattered light signals are evaluated using the Fraunhofer method.

It is furthermore preferred that the average thickness ($h_{50}$) of the coated aluminum effect pigments according to the invention is preferably in a range of from about 150 nm to about 2.5 μm, preferably from about 170 nm to about 2.1 μm, still further preferably from about 185 nm to about 1.6 μm, still further preferably from about 200 nm to about 1.4 μm. The term "average thickness" or "$h_{50}$" in the context of the invention relates to the arithmetic mean of the thicknesses of at least 50 aluminum effect pigments which have been determined by means of scanning electron microscopy (SEM), wherein the best possible orientation of the aluminum effect pigments according to the invention in the application medium is to be ensured. For this, the metal effect pigments can be pretreated by suitable additives beforehand. The cured application medium is then polished and the polished cross-section is observed in SEM after conventional sample preparation. Only particles which have a good orientation are selected for the count. The average thickness or the $h_{50}$ value relates to the aluminum effect pigment according to the invention.

In further preferred embodiments the aluminum effect pigments according to the invention furthermore have a relative width, determined via thickness counting by scanning electron microscopy (SEM), of the thickness distribution Δh which is calculated with the aid of the corresponding continuous cumulative curve of the relative frequency according to the formula $$\Delta h = (h_{90} - h_{10})/h_{50}$$

of from 0.3 to 0.9, preferably from 0.35 to 0.85 and particularly preferably from 0.4 to 0.8.

For specific uses with particular requirements, however, it can also be preferred to use PVD aluminum effect pigments. Due to the significantly higher costs of such pigments, however, it is usually preferred that the pigments used in the method according to the invention have been obtained by grinding. The aluminum effect pigments according to the invention consequently preferably contain an aluminum effect pigment obtained by grinding.

Preferably, aluminum effect pigments obtained by grinding aluminum grit are thus used in the wet-chemical oxidation.

The aluminum grit can have, for example, a size distribution having a $D_{grit,50}$ of from 1 to 210 μm and a $D_{grit,90}$ of from 2 to 450 μm. After the grinding, classification can be necessary in order to obtain the desired platelet-shaped aluminum effect pigment fraction. For the composition of the aluminum grit used, i.e. the purity and/or alloy constituents of aluminum alloys, reference is made to the above statements in connection with the aluminum effect pigments used in the wet-chemical oxidation. This disclosure of course also applies to the grit to be used for the production of the aluminum effect pigments.

The grinding of aluminum grit is predominantly carried out as wet grinding. Here, the aluminum grit is ground in ball mills, preferably in several grinding stages under different grinding conditions, such as, for example, size, diameter and speed of rotation of the mill, ball size, grinding duration with the addition of lubricants, such as, for example, stearic or oleic acid, to prevent cold welding of the aluminum effect pigments, a solvent and with grinding bodies, such as e.g. steel balls. White spirit or solvent naphtha, for example, can be used as solvents. The use of alcohols, such as e.g. isopropanol, ketones, esters, ethers, etc. is also possible. After the grinding and optional classification, the uncoated aluminum effect pigments are collected in various containers and then homogenized or mixed.

Further information on a grinding method which can be used here is to be found in WO 2009/152941 A2, to the disclosure of which reference is hereby made in full.

The term "form factor" in the context of the present invention denotes the size/thickness ratio or also aspect ratio. It is calculated from the ratio of the $D_{50}$ value to the $h_{50}$ value. In further embodiments, the form factor is in a range of from about 1,500:1 to about 2.5:1, preferably from about 900:1 to about 20:1, still further preferably in a range of from about 700:1 to about 30:1.

It is furthermore possible to vary the color properties of the pigments according to the invention by targeted coloring of the wet-chemically produced aluminum oxide layer. The hydrolysis reaction, preferably the sol-gel process, is carried out here in the presence of color pigments for application of the metal oxide layer which differs from aluminum oxide, preferably silicon oxide layer. Due to the targeted production of a metal oxide layer in which corresponding color pigments are enclosed, the most diverse color shades, such as e.g. blue, red and violet, can be generated.

The amount of color pigment here is preferably 5 to 40 wt.-%, relative to the weight of the non-oxidized aluminum effect pigments. Organic color pigments, inorganic color pigments or mixtures thereof can be used as color pigments. Color pigments which are characterized by a high color fastness are preferred. Examples of color pigments which are suitable for the use according to the invention are C.I. Pigment Red 202C.I., C.I. Pigment Red 179, C.I. Pigment Red 101 and Pigment Blue 15:3.

In particular embodiments it has furthermore proved advantageous to add an additive to improve the pigment dispersibility, such as, for example, Antiterra U 80 from Byk-Chemie.

In further embodiments in which, for example, the stability of the metal oxide layer which differs from aluminum oxide is to the fore, it is preferred that larger amounts of color pigments are not present in the reaction solution during the application of the metal oxide layer which differs from aluminum oxide. In particular, in further embodiments it is preferred that the corresponding reaction mixtures and subsequently the metal oxide layers, which differ from aluminum oxide, of the wet-chemically oxidized aluminum effect pigments according to the invention contain substantially no color pigments, preferably less than 1 wt.-% color pigments, more preferably less than 0.1 wt.-% color pigments and still more preferably less than 0.01 wt.-% color pigments, in each case relative to the weight of the wet-chemically oxidized aluminum effect pigments used. In particular, in others of the abovementioned embodiments it is preferred that no color pigments are present during the application of the metal oxide layer which differs from aluminum oxide, or that the metal oxide layer which differs from aluminum oxide and is to be applied according to the invention contains no color pigments. Without being understood as limiting the invention, it is the opinion of the inventors that such additional small particles impede the penetration of the educts used for the production of the metal oxide layer into the pores of the wet-chemically produced aluminum oxide layer and the formation of a metal oxide layer of deteriorated quality can be possible.

According to a variant of the invention, it is preferred, for example, that the wet-chemically oxidized aluminum effect pigments have at least one metal oxide layer which differs from aluminum oxide and at least one enveloping organic polymer layer; that the weight ratio of the metal oxide, which differs from aluminum oxide and is applied as metal oxide layer, to the wet-chemically produced aluminum oxide layer is in a range of from 1:1 to 1:40; that the sum of the at least one metal oxide layer which differs from aluminum oxide and the at least one organic polymer layer is in the range of from 10 to 50 wt.-%, relative to the total weight of the uncoated, wet-chemically oxidized aluminum effect pigments; and that the weight ratio of the at least one metal oxide layer which differs from aluminum oxide to the at least one organic polymer layer is in a range of from 1:2 to 1:20. In particular embodiments of the abovementioned variant it is preferred in particular that the amount of the at least one metal oxide layer which differs from aluminum oxide is in a range of from 0.8 wt.-% to 20 wt.-%, relative to the total weight of the uncoated, wet-chemically oxidized aluminum effect pigments; and that the at least one metal oxide layer, which differs from aluminum oxide, of the aluminum effect pigments according to the invention substantially consists of metal oxide which is selected from the group consisting of silicon oxide, boron oxide, zirconium oxide, titanium oxide, oxide hydrates thereof, hydroxides thereof and mixtures thereof.

According to a further variant of the invention, it is preferred, for example, that the wet-chemically oxidized aluminum effect pigments have at least one metal oxide layer which differs from aluminum oxide and at least one enveloping organic polymer layer; that the weight ratio of the metal oxide, which differs from aluminum oxide and is applied as metal oxide layer, to the wet-chemically produced aluminum oxide layer is in a range of from 1:2 to 1:25; that the sum of the at least one metal oxide layer which differs from aluminum oxide and the at least one organic polymer layer is in the range of from 10 to 50 wt.-%, relative to the total weight of the uncoated, wet-chemically oxidized aluminum effect pigments; and that the weight ratio of the at least one metal oxide layer which differs from aluminum oxide to the at least one organic polymer layer is in a range of from 1:2 to 1:20. In particular embodiments of the abovementioned variant, it is preferred in particular that the average pigment diameter ($D_{50}$) of the aluminum effect pigments according to the invention is in a range of from 1 µm to 180 µm; that the average thickness ($h_{50}$) of the aluminum effect pigments according to the invention is in a range of from 150 nm to 2.5 µm; and that the form factor of the aluminum effect pigments according to the invention is in a range of from about 1,500:1 to about 2.5:1.

According to a variant of the invention, for example, it is preferred that the wet-chemically oxidized aluminum effect pigments have at least one metal oxide layer which differs from aluminum oxide and at least one enveloping organic polymer layer; that the weight ratio of the metal oxide, which differs from aluminum oxide and is applied as metal oxide layer, to the wet-chemically produced aluminum oxide layer is in a range of from 1:1 to 1:40; that the sum of the at least one metal oxide layer which differs from aluminum oxide and the at least one organic polymer layer is in the range of from 10 to 50 wt.-%; that the weight ratio of the at least one metal oxide layer which differs from aluminum oxide to the at least one organic polymer layer is in a range of from 1:2 to 1:20; that the amount of the at least one metal oxide layer which differs from aluminum oxide is in a range of from 0.8 wt.-% to 20 wt.-%; and that the amount of the at least one organic polymer layer of the aluminum effect pigments according to the invention is in a range of from 8 to 40 wt.-%; wherein the abovementioned wt.-% are relative to the total weight of the uncoated, wet-chemically oxidized aluminum effect pigments.

According to a variant of the invention, for example, it is preferred that the wet-chemically oxidized aluminum effect pigments have at least one metal oxide layer which differs from aluminum oxide and at least one enveloping organic polymer layer; that the weight ratio of the metal oxide, which differs from aluminum oxide and is applied as metal oxide layer, to the wet-chemically produced aluminum oxide layer is in a range of from 1:1 to 1:40; that the thickness of the wet-chemically produced aluminum oxide layer is in a range of from 45 nm to 210 nm; and that the elemental aluminum content of the aluminum effect pigments according to the invention is in a range of from 31 to 77 wt.-%, relative to the total weight of the uncoated, wet-chemically oxidized aluminum effect pigments.

The present invention furthermore relates to the use of the aluminum effect pigments according to the invention, which can be used, for example, for coloring. Thus, the aluminum effect pigments according to the invention can be incorporated, for example, into a coating agent. Examples of coating agents are varnishes, such as coil coating varnishes; varnish concentrates; printer inks; printer ink concentrates; paints; paint concentrates; powder coatings or powder coating concentrates. The aluminum effect pigments according to the invention can furthermore be incorporated into a material, such as, for example, a plastic. The aluminum effect pigments according to the invention here can also provide functional properties, in addition to optical properties, for example can serve as a laser marking additive in plastics. In addition, the pigments according to the invention can be used, for example, in cosmetics.

The aluminum effect pigments according to the invention can be used in cosmetic formulations in combination with raw materials, auxiliary substances and active ingredients which are suitable for the respective use. For example, the aluminum effect pigments according to the invention can be used in body powder, face powder, compact and loose powder, face makeup, powder cream, cream makeup, emulsion makeup, wax makeup, foundation, mousse makeup, rouge, eye makeup, such as eyeshadow, mascara, eyeliner, liquid eyeliner, eyebrow pencil, lip care stick, lipstick, lip gloss, lip liner, hair styling compositions, such as hairspray, hair mousse, hair gel, hair wax, hair mascara, permanent or semi-permanent hair colors, temporary hair colors, skincare compositions, such as lotions, gels, emulsions, and nail polish compositions. The concentration of the aluminum effect pigments according to the invention in the formulation here is preferably between 0.001 wt.-% for rinse-off products and 40.0 wt.-% for leave-on products.

In addition to the raw materials, auxiliary substances and active ingredients, further colorants, conventional effect pigments or mixtures of these can furthermore also be used in the cosmetic formulations in variable proportions. For example, commercially available pearlescent pigments based on natural mica coated with high refractive index metal oxides (such as e.g. the pearlescent pigments of the Prestige product group from Eckart), BiOCl platelets, $TiO_2$ platelets, pearlescent pigments based on synthetic mica coated with high refractive index metal oxides or based on glass platelets coated with high refractive index metal oxides (such as e.g. the pearlescent pigments of the MIRAGE product group from Eckart), $Al_2O_3$, $SiO_2$ or $TiO_2$ platelets, can be used in combination or in a mixture with the aluminum effect pigments according to the invention. Furthermore, metal effect pigments, such as e.g. the pearlescent pigments of the Visionaire product group from Eckert, can also be added. Furthermore, for example, the colorants can be selected from inorganic or organic pigments.

In further embodiments it is preferred in particular that the pigments according to the invention for use in cosmetic formulations have a high refractive index metal chalcogenide layer, preferably a high refractive index metal oxide layer, such as, for example, an iron oxide layer, in addition to the at least one metal oxide layer, in particular silicon oxide layer.

The pigments according to the invention can furthermore be introduced into a coating agent, such as, for example, a varnish, such as e.g. a coil coating varnish, a varnish concentrate, a printer ink, a printer ink concentrate, a paint, a paint concentrate, a powder coating or a powder coating concentrate.

For application as a powder coating in particular, the pigments according to the invention have additionally proved to be very suitable, since only with the coating to be applied according to the invention having a metal oxide which differs from aluminum oxide and an enveloping polymer layer was a satisfactory applicability of the wet-chemically oxidized aluminum effect pigments achieved, as illustrated in Example 1 according to the invention.

It has furthermore been shown, surprisingly, that regardless of the large amount of water which should still always be present finely dispersed in, for example, a metal oxide layer produced by means of the sol-gel process, the pigments according to the invention can be applied by means of the coil coating method or powder coating, and stoved, without bubbles or defects in the varnish layer applied arising due to an after-oxidation.

The aluminum effect pigments according to the invention are particularly suitable, for example, for automobile bodies, façade elements, printed matter, such as, for example, printed films, paper, cardboard boxes, plastics moldings etc. Preferably, the aluminum effect pigments according to the invention are used in powder coatings, coil coating formulations, water varnishes and polymers or plastics. In further preferred embodiments, the coating agent is a powder coating or a varnish for use in the coil coating method.

Powder coating is a versatile electrostatic method for coating batch products which is often used in industrial manufacture. In addition to the absence of solvent and the possibility of re-using the overspray, the method furthermore offers various advantages, such as the applied powder being encompassing. The powder coating applied here contains binders, the aluminum effect pigments according to the invention, fillers and crosslinking agents as well as, optionally, additives. According to the invention, by a binder is meant the definition stated in DIN 55 945. That is to say, the binder includes both the film-forming agent and non-volatile auxiliary substances, such as plasticizers and desiccants. After application of the powder coating, a curing step by means of stoving or radiation energy is carried out.

The production of corresponding powder coatings can be carried out in various ways. In the mixing method, the aluminum effect pigment according to the invention is already added before extrusion and grinding. As a consequence of the shearing forces which arise, damage to or destruction of, in particular, platelet-shaped pigments can occur here. This in turn leads to an impairment of the gloss and the optical properties in a coating produced by this means.

Corresponding powder coatings can furthermore be produced by means of the dry blend method. Here, the aluminum effect pigments according to the invention are added only after the extrusion and grinding. This has the disadvantages, however, that a separation as a consequence of different electrostatic charging during application of the varnish can give rise to an inhomogeneous coating. Furthermore, a depletion or accumulation of the pigment can occur both during transportation and storage and in the overspray, with the result that a renewed use of this material is prevented. It is therefore preferred to combine the dry blend method with the bonding method. Here, the pigment is bonded to the particles of the base varnish by heating. This method of production delivers powder coatings of higher quality with, for example, good recyclability of the overspray, but is relatively cost-intensive. The most inexpensive powder coatings are therefore produced by means of the mixing method.

A further coating method which is often used in industrial manufacture is the coil coating method. In this environmentally friendly method an application efficiency of almost 100% can be achieved by an optimized process control, whereas otherwise in most varnishing methods, for example, larger losses arise due to the overspray.

The aluminum effect pigments according to the invention can furthermore be incorporated into plastics. Thermoplastic, thermosetting or elastomeric plastics, for example, are used here. In particular, in further embodiments it is preferred to incorporate the aluminum effect pigments according to the invention into thermoplastics. In principle there are no limitations with respect to the thermoplastics known to a person skilled in the art. Information on this can be found in a wide range of specialist books or the specialist literature. On the basis of the respectively planned intended use, however, particular thermoplastics can be preferred or of less interest.

Examples of suitable thermoplastics are polyoxyalkylenes, polycarbonates (PC), polyesters, such as polybutylene terephthalate (PBT) or polyethylene terephthalate (PET), polyolefins, such as polyethylene or polypropylene (PP), poly(meth)acrylates, polyamides, vinylaromatic (co)polymers, such as polystyrene, impact-modified polystyrene, such as HI-PS, or ASA, ABS or AES polymers, polyarylene ethers, such as polyphenylene ether (PPE), polysulfones, polyurethanes, polylactides, halogen-containing polymers, polymers containing imide groups, cellulose esters, silicone polymers or thermoplastic elastomers. In addition, it is possible to use mixtures of different thermoplastics in the form of so-called single- or multi-phase polymer blends.

Polyoxyalkylene homo- or copolymers, in particular (co)polyoxymethylenes (POM), are commercially obtainable and are marketed, for example, under the trade name Ultraform (BASF SE, Germany). Quite generally, these plastics have at least 50 mol.-% recurring units of —CH$_2$O— in the polymer main chain. Homopolymers which are preferred as plastics are obtained, in particular, by polymerization of formaldehyde or trioxane, preferably in the presence of corresponding catalysts. Polyoxymethylene copolymers and polyoxymethylene terpolymers are preferred. The preferred polyoxymethylene (co)polymers have melting points of at least 150° C. and molecular weights (weight-average value) M in the range of from 5,000 to 200,000, preferably from 7,000 to 150,000 g/mol. Polyoxymethylene polymers which are end-group-stabilized and have C—C bonds at the chain ends are particularly preferred.

Polycarbonates can be produced, for example, by means of interfacial polycondensation or by reaction of biphenyl carbonate with bisphenols. 2,2-Di(4-hydroxyphenyl)propane (bisphenol A), for example, can be used as the bisphenol here. They are commercially obtainable and are marketed, for example, under the trade name Lexan® (GE Plastics B.V., Holland).

Polyesters are produced by the reaction of aromatic dicarboxylic acids, esters thereof or other ester-forming derivatives with aliphatic dihydroxy compounds. The aromatic ring contained in the main chain can be substituted, e.g. by halogen, such as chlorine and bromine, or by C$_1$-C$_4$-alkyl groups, such as methyl, ethyl, i- or n-propyl and n-, i- or tert-butyl groups. Examples of dicarboxylic acids are naphthalenedicarboxylic acid, terephthalic acid and isophthalic acid or mixtures thereof. Up to 10 mol.-% of the aromatic dicarboxylic acids can be replaced by aliphatic or cycloaliphatic dicarboxylic acids, such as adipic acid, azelaic acid, sebacic acid, dodecandioic acids and cyclohexanedicarboxylic acids. The following are used, for example, as aliphatic dihydroxy compounds: diols having 2 to 6 carbon atoms, such as 1,2-ethanediol, 1,4-butanediol, 1,6-hexanediol, 1,4-hexanediol, 1,4-cyclohexanediol and neopentyl glycol or mixtures thereof. Examples of polyesters which can be used are polyethylene terephthalate (PET), polyethylene naphthalate and polybutylene terephthalate (PBT), which are obtainable, for example, under the trade names Rynite® (PET; DuPont, USA) or Ultradur® (PBT; BASF SE).

Polyolefins, such as polyethylenes, polypropylenes or copolymers based on ethylene or propylene are obtainable under the trade names Lupolen® and Novolen® respectively.

The poly(meth)acrylates include in particular polymethyl methacrylate (PMMA) and copolymers based on methyl methacrylate with up to 40 wt.-% further copolymerizable monomers, such as n-butyl acrylate, t-butyl acrylate or 2-ethylhexyl acrylate. Such polymers are marketed, for example, under the trade names Lucryl® (BASF SE) and Plexiglas® (Röhm GmbH, Germany). In the context of the invention, by these are also meant impact-modified poly(meth)acrylates and mixtures of poly(meth)acrylates and SAN polymers which are impact-modified with polyacrylate rubbers (e.g. the commercial product Terlux® from BASF SE).

Examples of the polyamides are polycaprolactam, polycapryllactam, polylaurolactam and polyamides which are obtained by reaction of dicarboxylic acids with diamines, and also include, for example, polyetheramides, such as polyether block amides. In particular, for example, polyhexamethyleneadipic acid amide (PA 66, Ultramid® A from BASF SE) and polyhexamethylenesebacic acid amide (PA 610, Nylon® 610 from DuPont), polycaprolactam (PA 6, Ultramid® B from BASF SE) and copolyamides 6/66, in particular with a proportion of caprolactam units (Ultramid® C from BASF SE) of from 5 to 95 wt.-% can.

Examples of vinylaromatic (co)polymers are polystyrene, styrene-acrylonitrile copolymers (SAN) and impact-modified polystyrene (HIPS=high impact polystyrene). Preferably not more than 20 wt.-%, in particular not more than 8 wt.-%, of the monomers here can also be replaced by comonomers, such as (meth)acrylonitrile or (meth)acrylic acid ester. Further examples are particularly preferably ASA, ABS and AES polymers (ASA=acrylonitrile-styrene-acrylic ester, ABS=acrylonitrile-butadiene-styrene, AES=acrylonitrile-EPDM rubber-styrene). These impact-modified vinylaromatic polymers contain at least one rubber-elastic graft polymer and one thermoplastic polymer (matrix polymer).

The polyarylene ethers also include, inter alia, polyarylene ether sulfides, polyarylene ether sulfones or polyarylene ether ketones, wherein the arylene groups can be identical or different and independently of each other represent an aromatic radical having 6 to 18 C atoms. Corresponding polymers are commercially obtainable, for example, under the trade name Noryl® (GE Plastics B.V., Holland).

Polyurethanes, polyisocyanurates and polyureas and the production thereof, for example by reaction of isocyanates with compounds which are reactive towards isocyanates, are known to a person skilled in the art. Corresponding polymers are obtainable, for example, under the name Elastolan® (Elastogran GmbH, Germany).

Polylactides are polymers of lactic acid, but in the context of the present invention in principle also include co- or block copolymers based on lactic acid and further monomers. In further embodiments, however, it is preferred in particular that the monomers of the polylactides are essentially lactic acid.

Examples of halogen-containing polymers are polyvinyl chloride (PVC), such as rigid PVC and plasticized PVC, and copolymers of vinyl chloride, such as PVC-U molding compounds.

Examples of fluorine-containing polymers are polytetrafluoroethylene (PTFE), tetrafluoroethylene-perfluoropropylene copolymers (FEP), copolymers of tetrafluoroethylene with perfluoroalkyl vinyl ethers, ethylene-tetrafluoroethylene copolymers (ETFE), polyvinylidene fluoride (PVDF), polyvinyl fluoride (PVF), polychlorotrifluoroethylene (PCTFE) and ethylene-chlorotrifluoroethylene copolymers (ECTFE).

Polymers containing imide groups are, in particular, polyimides, polyether-imides and polyamide-imides.

Examples of cellulose esters are cellulose acetate, cellulose acetobutyrate and cellulose propionate.

Examples of the silicone polymers are, in particular, silicone rubbers. These are usually polyorganosiloxanes which have groups which are capable of crosslinking reactions.

The thermoplastic elastomers can be processed like thermoplastics, but also have elastoplastic properties. Examples are thermoplastic polyurethane elastomers (TPE-U or TPU), styrene oligo-block copolymers (TPE-S), such as SBS (styrene-butadiene-styrene-oxy block copolymer) and SEES (styrene-ethylene-butylene-styrene block copolymer, obtainable by hydrogenation of SBS), thermoplastic polyolefin elastomers (TPE-O), thermoplastic polyester elastomers (TPE-E), thermoplastic polyamide elastomers (TPE-A) and in particular thermoplastic vulcanizates (TPE-V).

In addition to the pigments according to the invention, the abovementioned plastics can contain usual additives. These additives can be selected, for example, from the group consisting of fillers, additives, plasticizers, lubricants or mold release agents, impact modifiers, color pigments, dyestuffs, flame retardants, antistatics, optical brighteners, antioxidants, antimicrobially active biostabilizers, chemical blowing agents, organic crosslinking agents and other additives and mixtures thereof.

The coloring effect is only very weak below 0.1 wt.-% of the aluminum effect pigments according to the invention, relative to the total weight of the plastic containing the aluminum effect pigments according to the invention. It has furthermore been found that the mechanical strength of a corresponding plastic decreases if the amount of pigment is too high. According to further preferred embodiments, the proportion of the aluminum effect pigments according to the invention in the plastic is in a range of from 0.01 to 12 wt.-%, preferably from 0.1 to 9 wt.-%, more preferably from 0.25 to 5 wt.-%, still more preferably from 0.5 to 2.5 wt.-%, in each case relative to the total weight of the plastic containing the aluminum effect pigments according to the invention.

However, if the according to the invention are used, for example, not for coloring a plastic but for laser marking, other concentrations of the aluminum effect pigment according to the invention can be preferred. In laser marking, a laser beam heats aluminum effect pigments according to the invention contained in the plastic, as a consequence of which a visible change in the plastic is brought about by foaming or carbonization. Since for this purpose usually no optical impairment of the plastic is desired, in many embodiments, for example, a concentration of at most 0.8 wt.-% is preferred, relative to the total weight of the plastic comprising the aluminum effect pigment according to the invention. Below an amount of 0.0005 wt.-%, relative to the total weight of the plastic comprising the aluminum effect pigment according to the invention, however, the effects brought about by means of laser marking are only very weak. In further embodiments it is therefore preferred that the concentration of the aluminum effect pigment according to the invention is 0.0005 to 0.8 wt.-%, preferably 0.001 to 0.6 wt.-% and still further preferably 0.005 to 0.55 wt.-%, in each case relative to the total weight of the plastic comprising the aluminum effect pigment according to the invention.

It has been shown, however, that some particularly advantageously used reactants are not compatible with cosmetics. In particular, in further embodiments it is therefore preferred that the uses do not include cosmetic use. Furthermore, in further embodiments the pigments according to the invention comprise substances which are unsuitable for cosmetic use.

The method according to the invention comprises the following steps:

(1) wet-chemical oxidation of aluminum effect pigments,
(2) coating of the wet-chemically oxidized aluminum effect pigments obtained in step (1) with metal oxide which differs from aluminum oxide, wherein the weight ratio of the metal oxide, applied as at least one metal oxide layer, to the aluminum oxide layer produced wet-chemically in step (1) is in a range of from 1:1 to 1:40,
(3) coating of the wet-chemically oxidized aluminum effect pigments, coated with metal oxide and obtained in step (2), with at least one enveloping organic polymer layer.

The method step for application of the metal oxide layer comprises at least one hydrolysis and condensation reaction. In particular, the sol-gel method is preferred here. Metal halides, such as metal chlorides, or metal alcoholates, for example, can be used as the metal oxide source for production of the at least one metal oxide layer.

In particular, in further embodiments it is preferred that the at least one metal oxide layer is produced by means of the sol-gel process. Here, corresponding metal alcoholates are hydrolyzed by water, wherein acids or bases are preferably used as catalysts. A condensation reaction subsequently starts, in which a metal oxide coating is formed. Preferably, metal alcoholates are used in the sol-gel process according to the invention, but substances such as, for example, waterglass can also be used.

The metal alcoholates to be used according to the invention in the sol-gel process preferably carry alkoxy groups, which are selected from the group consisting of methoxy groups, ethoxy groups, propoxy groups, butoxy groups, pentoxy groups and mixtures thereof. The alkoxy groups are extremely preferably methoxy groups, ethoxy groups or mixtures thereof.

For simplification of the course of the reaction, it is preferred that the hydrolysis reaction for production of the metal oxide layer proceeds in the reaction medium of the wet-chemical oxidation reaction. However, it is also possible to isolate the wet-chemically oxidized aluminum effect pigments, for example by means of filtration or centrifugation, and to disperse them in another solvent.

The hydrolysis reaction, preferably the sol-gel process, is usually carried out in an organic solvent in the presence of small amounts of water, such as, for example, 1 to 9 vol.-%, preferably 2 to 4 vol.-% water, relative to the total volume of the water-containing organic solvent. The water can already be contained here in the organic solvent, or can be added at a later point in time. Acids or bases are usually added as catalysts.

Alcohols, glycols, esters, ketones and mixtures of these solvents are preferably used as organic solvents, more preferably alcohols, glycols, and ketones which are liquid at room temperature. The use of alcohols, glycols or mixtures thereof is particularly suitable. Alcohols are particularly preferably used.

The alcohol is preferably selected from the group consisting of methanol, ethanol, isopropanol, n-propanol, t-butanol, n-butanol, isobutyl alcohol, pentanol, hexanol and mixtures thereof. Ethanol and isopropanol have proved to be very suitable. In further embodiments it is preferred that ethanol or isopropanol is used as the solvent.

Preferred glycols are butyl glycol, propyl glycol, ethylene glycol or mixtures thereof.

Organic acids, inorganic acids or mixtures thereof, for example, can be used as the catalyst. Organic acids are preferably selected from the group consisting of formic acid, acetic acid, propionic acid, oxalic acid, malonic acid, maleic acid, succinic acid, anhydrides of the named acids and mixtures thereof. Formic acid, acetic acid, oxalic acid or mixtures thereof are particularly preferred. Inorganic acids are preferably selected from the group consisting of nitric acid, sulfuric acid, phosphoric acid, hydrochloric acid, boric acid, hydrofluoric acid and mixtures thereof. Nitric acid, hydrofluoric acid or mixtures thereof are particularly preferred.

A wide range of bases known to a person skilled in the art can be used as basic catalysts, preferably nitrogen-containing bases, in particular amines. These can be primary, secondary or tertiary amines.

According to a preferred embodiment, the amine is selected from the group consisting of dimethylethanolamine (DMEA), monoethanolamine (MEA), diethanolamine (DEA), triethanolamine (TEA), ethylenediamine (EDA), t-butylamine, monomethylamine, dimethylamine, trimethylamine, monoethylamine, diethylamine, triethylamine, diethylenetriamine, diisopropylethylamine, pyridine, pyridine derivatives, aniline, aniline derivatives, choline, choline derivatives, urea, urea derivative, hydrazine derivatives and mixtures thereof.

Ethylenediamine, monoethylamine, diethylamine, monomethylamine, dimethylamine, triethylamine or mixtures thereof have proved to be very suitable as basic aminic catalyst.

Inorganic bases, such as ammonia, hydrazine, sodium hydroxide, potassium hydroxide, ammonium hydroxide, ammonium carbonate, ammonium bicarbonate, sodium carbonate, sodium bicarbonate, potassium carbonate, sodium bicarbonate or mixtures thereof, can of course also be used. Ammonia, hydrazine or mixtures thereof have proved to be very suitable.

According to an extremely preferred embodiment, tetraalkoxysilane is used as a metal alkoxide. Tetramethoxysilane, tetraethoxysilane, tetraisopropoxysilane or condensates thereof or mixtures thereof are preferably used as the tetraalkoxysilane. Tetraethoxysilane, oligomers of tetraethoxysilane or mixtures thereof have proved to be very suitable.

The application of the at least one organic polymer layer is preferably carried out here by polymerization of suitable monomers or oligomers. The monomers or oligomers can have functionalities which are selected from the group consisting of amino, hydroxyl, thiol, epoxy, acrylate, methacrylate, vinyl, allyl, alkenyl, alkynyl, carboxyl, carboxylic anhydride, isocyanate, cyanate, ureido, carbamate, ester groups and mixtures thereof.

As educts of the organic polymer layer, in particular crosslinking, i.e. polyfunctional, (meth)acrylates are suitable, as monomers or reactive oligomers or polymers. Examples of such compounds are: allyl methacrylate, bisphenol A dimethacrylate, 1,3-butanediol dimethacrylate, 1,4-butanediol dimethacrylate, ethylene glycol dimethacrylate, 1,6-hexanediol diacrylate, 1,6-hexanediol dimethacrylate, diethylene glycol dimethacrylate, diurethane dimethacrylate, dipropylene glycol diacrylate, 1,12-dodecanediol dimethacrylate, ethylene glycol dimethacrylate, methacrylic anhydride, N,N-methylene-bis-methacrylamide, neopentyl glycol dimethacrylate, polyethylene glycol dimethacrylate, polyethylene glycol 200 diacrylate, polyethylene glycol 400 diacrylate, polyethylene glycol 400 dimethacrylate, tetraethylene glycol diacrylate, tetraethylene glycol dimethacrylate, tricyclodecanedimethanol diacrylate, tripropylene glycol diacrylate, triethylene glycol dimethacrylate, pentaerythritol triacrylate, trimethylolpropane triacrylate, trimethylolpropane trimethacrylate, tris-(2-hydroxyethyl) isocyanurate triacrylate, pentaerythritol tetraacrylate, dipentaerythritol pentaacrylate or mixtures thereof.

In further embodiments, the use of trifunctional and higher-functional (meth)acrylates, in particular trifunctional (meth)acrylates, is preferred. The term "(meth)acrylate" in the context of the present invention includes methacrylates and acrylates.

In further embodiments, the curing or polymerizing-out of vinyl- and/or (meth)acrylate-functional monomers in the production of the at least one organic polymer layer is carried out thermally.

In further preferred embodiments, the curing or polymerizing-out is carried out by radical polymerization using polymerization starters, preferably radical initiators. These are commercially available, as a rule organic or inorganic peroxides or diazonium compounds. Examples of such compounds are: acetyl-cyclohexane-sulfonyl peroxide, bis(2,4-dichlorobenzoyl) peroxide, diisononanyl peroxide, dioctanoyl peroxide, diacetyl and dibenzoyl peroxide; peroxydicarbonates (e.g. diisopropyl peroxydicarbonate, di-n-butyl peroxydicarbonate, di-2-ethylhexyl peroxydicarbonate, dicyclohexyl peroxydicarbonate), alkyl peresters (e.g. cumyl perneodecanoate, t-butyl perneodecanoate, t-amyl perpivalate, t-butyl per-2-ethylhexanoate, t-butyl perisobutyrate, t-butyl perbenzoate), dialkyl peroxides (e.g. dicumyl peroxide, t-butyl-cumyl peroxide, 2,5-dimethylhexane-2,5-di-t-butyl peroxide, di(t-butylperoxyisopropyl)benzene, di-t-butyl peroxide, or 2,5-dimethylhex-3-yne-2,5-di-t-butyl peroxide), perketals (e.g. 1,1'-bis-(t-butylperoxy)-3,3,5-trimethylcyclohexanone peroxide, methyl isobutyl ketone peroxide, methyl ethyl ketone peroxide, acetylacetone peroxide), alkyl hydroperoxides (e.g. pinane hydroperoxide, cumene hydroperoxide, 2,5-dimethylhexane 2,5-dihydroperoxide or t-butyl hydroperoxide), azo compounds (e.g. 4,4'-azo-bis(4-cyanovaleric acid), 1,1'-azo-bis(cyclohexane-carboxylic acid nitrile), 1,1'-azo-bis(isobutyric acid amidine)dihydrochloride, 2,2'-azo-bis (isobutyronitrile), dimethyl 2,2'-azobis(2-methylpropionate)), or persulfates, such as sodium peroxodisulfate and potassium peroxodisulfate. 2,2'-Azo-bis(isobutyronitrile) and dimethyl-2,2'-azobis(2-methylpropionate) are preferred. These compounds are commercially obtainable from Aldrich Chemie, D-89552, Steinheim or Wako Chemicals GmbH, Fuggerstraβe 12, 41468 Neuss.

The educts of the at least one organic polymer layer can in particular also be reactive oligomers, polymers or mixtures thereof which are selected from the group consisting of polyacrylates, poly(meth)acrylates, polyethers, polyesters, polyamines, polyamides, polyols, polyurethanes, polyolefins and mixtures thereof.

According to a variant of the invention, the pigments according to the invention coated with metal oxide are dispersed in a, preferably organic, solvent and the suspension is brought to the reaction temperature. The educts of the organic polymer layer, for example in the form of organic monomers, reactive oligomers, reactive polymers or mixtures thereof, as well as, optionally, polymerization initiators are then added, for example by dropwise addition, as a result of which the organic polymer layer is formed on the pigments according to the invention. Preferably, the dispersion is stirred or agitated during the application of the organic polymer layer.

The organic polymer layer can of course also be applied by spraying on the educts, for example the organic monomers, reactive organic oligomers, reactive organic polymers or mixtures thereof, as well as, optionally, polymerization initiators in a fluidized bed in which the pigments according to the invention are fluidized.

According to a preferred variant of the invention, the coating is carried out in a liquid phase.

According to a further variant of the invention, the application of the enveloping organic polymer layer is carried out in the same solvent in which the metal oxide layer which differs from aluminum oxide has been applied. This method variant is a one-stage method variant, in contrast to the two-stage method variant described above.

After application of the organic polymer layer, these are preferably filtered out of the suspension.

According to a further variant of the invention, the application of the enveloping organic polymer layer to the metal oxide layer which differs from aluminum oxide is carried out in the form of a thermal polymerization without addition of an initiator. It has been observed that the thermal polymerization is suitable in particular for the formation of smooth surfaces.

In further embodiments according to the invention, the aluminum effect pigments according to the invention are pelletized, granulated, extrusion-granulated, extruded, briquetted or tableted and are consequently present in a substantially low-dust, preferably dust-free, compacted form. In these dosage forms the aluminum pigments according to the invention can be easily handled and simply incorporated into coating agents, such as, for example, varnishes, paints, printer inks, powder coatings, plastics, cosmetics etc.

According to a preferred variant, the pigments according to the invention are incorporated into a powder coating. According to a preferred variant of the invention, the enveloping organic polymer layer of the pigments according to the invention is compatible with the binder or binder system of the powder coating.

The invention is explained in more detail in the following with the aid of examples, without being limited thereto.

EXAMPLES

Example 1

Wet-Chemical Oxidation and Metal Oxide Coating

Comparison Example 1a 144 g of an aluminum effect pigment-white spirit paste ($D_{50}$: 20 μm; 69.3 wt.-% solids content, 30.7 wt.-% white spirit, corresponds to 100 g aluminum effect pigment) was dispersed in 200 g isopropanol and stirred for 30 min. 30 g water and 3 g ethylenediamine were then added and heated at 60° C. for 7 h. The metal oxide layer (silicon oxide layer) was subsequently applied to the reaction product, using 18.8 g tetraethoxysilane (TEOS) and 15 g water, wherein the reaction mixture was heated to 75° C. over 4 hours.

Organic Polymer Coating

Example 1b According to the Invention 139 g of the abovementioned wet-chemically oxidized aluminum effect pigments coated with silicon oxide (having a solids content of 57.73 wt.-%, corresponds to 80 g aluminum) were dispersed in 300 g isopropanol. Thereafter, 1.0 g methacryloxypropyltrimethoxysilane was added and the mixture was heated to 90° C. and stirred at this temperature for 1 h. Thereafter, a mixture consisting of: 0.9 g dimethyl 2,2'-azobis (2-methylpropionate) (trade name V 601; obtainable from WAKO Chemicals GmbH, Fuggerstraβe 12, 41468 Neuss), 17.5 g trimethylolpropane trimethacrylate and 5.8 g methacryloxypropyltrimethoxysilane, topped up to a volume of 144 ml with isopropanol, was metered in over a period of 3 h. Stirring was carried out at 90° C. for a further 3 h, and the product was isolated, dried and sieved with a sieve of 71-μm mesh width.

| Experiment no. | $SiO_2$ content | Plastic content | Ratio $SiO_2:Al_2O_3$ | Helos $D_{10}/D_{50}/D_{90}$ |
|---|---|---|---|---|
| Example 1b | 5.2 wt.-% | 22.7 wt.-% | 1:6.5 | 8.4/18.3/32.2 |

Example 2

Wet-Chemical Oxidation and Metal Oxide Coating

Comparison Example 2a 204 g of an aluminum effect pigment-white spirit paste ($D_{50}$: 15 μm; 68.8 wt.-% solids content, 31.2 wt.-% white spirit, corresponds to 140 g Al) was dispersed in 400 g isopropanol and stirred for 30 min. 70 g water and 5 g ethylenediamine were then added and heated to 60° C. for 7 h. The metal oxide layer (silicon oxide layer) was subsequently applied to the reaction product, using 68.5 g tetraethoxysilane (TEOS) and 90 g water, wherein the reaction mixture was heated to 75° C. over 4 hours.

Organic Polymer Coating

Example 2b According to the Invention 177 g of the abovementioned wet-chemically oxidized aluminum effect pigments coated with silicon oxide (having a solids content of 57 wt.-%, corresponds to 100 g aluminum effect pigment) were dispersed in 323 g isopropanol. Thereafter, 1.25 g methacryloxypropyltrimethoxysilane was added and the mixture was heated to 90° C. and stirred at this temperature for 1 h. Thereafter, a mixture consisting of: 1.12 g dimethyl 2,2'-azobis(2-methylpropionate) (trade name V 601; obtainable from WAKO Chemicals GmbH, Fuggerstraβe 12, 41468 Neuss), 21.9 g trimethylolpropane trimethacrylate and 7.25 g methacryloxypropyltrimethoxysilane, topped up to a volume of 180 ml with isopropanol, was metered in over a period of 3 h. Stirring was carried out at 90° C. for a further 3 h and the product was then isolated, dried and sieved with a sieve of 71-μm mesh width.

| Experiment no. | $SiO_2$ content | Plastic content | Ratio $SiO_2:Al_2O_3$ | Helos $D_{10}/D_{50}/D_{90}$ |
|---|---|---|---|---|
| Example 2b | 11.2 wt.-% | 28 wt.-% | 1:3.4 | 7.7/16.3/27.8 |

Example 3

Wet-Chemical Oxidation and Metal Oxide Coating

Comparison Example 3a 144 g of an aluminum effect pigment-white spirit paste ($D_{50}$: 20 μm; 69.3 wt.-% solids content, 30.7 wt.-% white spirit, corresponds to 100 g aluminum effect pigment) was dispersed in 200 g isopropanol and stirred for 30 min. 35 g water and 3.5 g ethylenediamine were then added and heated to 60° C. for 7 h. The metal oxide layer (silicon oxide layer) was subsequently applied to the reaction product, using 28.8 g tetraethoxysilane (TEOS) and 22.5 g water, wherein the reaction mixture was heated to 75° C. over 4 h.

Organic Polymer Coating

Example 3b According to the Invention 100 g of the abovementioned wet-chemically oxidized aluminum effect pigments coated with silicon oxide were dispersed in 400 g isopropanol. Thereafter, 1.25 g methacryloxypropyltrimethoxysilane was added and the mixture was heated to 90° C. and stirred at this temperature for 1 h. Thereafter, a mixture consisting of: 1.12 g dimethyl 2,2'-azobis(2-methylpropionate) (trade name V 601; obtainable from WAKO Chemicals GmbH, Fuggerstraße 12, 41468 Neuss), 21.9 g trimethylolpropane trimethacrylate and 7.25 g methacryloxypropyltrimethoxysilane, topped up to a volume of 180 ml with isopropanol, was metered in over a period of 3 h. Stirring was carried out at 90° C. for a further 3 h and the product was then isolated, dried and sieved with a sieve of 71-μm mesh width.

| Experiment no. | $SiO_2$ content | Plastic content | Ratio $SiO_2:Al_2O_3$ | Helos $D_{10}/D_{50}/D_{90}$ |
|---|---|---|---|---|
| Example 3b | 7.5 wt.-% | 26.1 wt.-% | 1:4.7 | 8.8/19.3/33.4 |

Example 4

Wet-Chemical Oxidation and Metal Oxide Coating

Comparison Example 4a 250 g of an aluminum effect pigment-white spirit paste ($D_{50}$: 20 μm; 70 wt.-% solids content, 30 wt.-% white spirit, corresponds to 175 g aluminum effect pigment) was dispersed in 800 g isopropanol and stirred for 30 min. 100 g water and 5.6 g ethylenediamine were then added and heated to 60° C. for 7 h. The metal oxide layer (silicon oxide layer) was subsequently applied to the reaction product, using 55.2 g TEOS and 22.5 g water, wherein the reaction mixture was heated to 75° C. over 4 h.

Organic Polymer Coating

Example 4b According to the Invention 100 g of the abovementioned wet-chemically oxidized aluminum effect pigments coated with silicon oxide were dispersed in 400 g isopropanol. Thereafter, 1.25 g methacryloxypropyltrimethoxysilane was added and the mixture was heated to 90° C. and stirred at this temperature for 1 h. Thereafter, a mixture consisting of: 1.12 g dimethyl 2,2'-azobis(2-methylpropionate) (trade name V 601; obtainable from WAKO Chemicals GmbH, Fuggerstraße 12, 41468 Neuss), 21.9 g trimethylolpropane trimethacrylate and 7.25 g methacryloxypropyltrimethoxysilane, topped up to a volume of 180 ml with isopropanol, was metered in over a period of 3 h. Stirring was carried out at 90° C. for a further 3 h and the product was then isolated, dried and sieved with a sieve of 71-μm mesh width.

| Experiment no. | $SiO_2$ content | Plastic content | Ratio $SiO_2:Al_2O_3$ |
|---|---|---|---|
| Example 4b | 7.3 wt.-% | 28.7 wt.-% | 1:4.7 |

Example 5

Wet-Chemical Oxidation and Metal Oxide Coating

Comparison Example 5a 250 g of an aluminum effect pigment-white spirit paste ($D_{50}$: 20 μm; 70 wt.-% solids content, 30 wt.-% white spirit, corresponds to 175 g aluminum effect pigment) was dispersed in 800 g isopropanol and stirred for 30 min. 100 g water and 10 g triethylamine were then added and heated to 60° C. for 7 h. The metal oxide layer (silicon oxide layer) was subsequently applied to the reaction product, using 55.2 g TEOS and 22.5 g water, wherein the reaction mixture was heated to 75° C. over 4 h.

Organic Polymer Coating

Example 5b According to the Invention 100 g of the abovementioned wet-chemically oxidized aluminum effect pigments coated with metal oxide were dispersed in 400 g isopropanol. Thereafter, 1.25 g methacryloxypropyltrimethoxysilane were added and the mixture was heated to 90° C. and stirred at this temperature for 1 h. Thereafter, a mixture consisting of: 1.12 g dimethyl 2,2'-azobis(2-methylpropionate) (trade name V 601; obtainable from WAKO Chemicals GmbH, Fuggerstraße 12, 41468 Neuss), 21.9 g trimethylolpropane trimethacrylate and 7.25 g methacryloxypropyltrimethoxysilane, topped up to a volume of 180 ml with isopropanol, was metered in over a period of 3 h. Stirring was carried out at 90° C. for a further 3 h and the product was then isolated, dried and sieved with a sieve of 71-μm mesh width.

| Experiment no. | $SiO_2$ content | Plastic content | Ratio $SiO_2:Al_2O_3$ |
|---|---|---|---|
| Example 5b | 7.3 wt.-% | 28.7 wt.-% | 1:5.2 |

Example 6

Wet-Chemical Oxidation and Metal Oxide Coating

Comparison Example 6a 286 g of an aluminum effect pigment-white spirit paste ($D_{50}$: 15 μm; 70.0 wt.-% solids content, 30 wt.-% white spirit, corresponds to 200 g aluminum effect pigment) was dispersed in 850 g isopropanol and stirred for 30 min. 110 g water and 12 g triethylamine were then added and heated to 60° C. for 7 h. The metal oxide layer (silicon oxide layer) was subsequently applied to the reaction product, using 68.5 g tetraethoxysilane (TEOS) and 28 g water, wherein the reaction mixture was heated to 75° C. over 4 hours.

Organic Polymer Coating

Example 6b According to the Invention 178 g of the abovementioned wet-chemically oxidized aluminum effect pigments coated with silicon oxide (having a solids content of 56 wt.-%, corresponds to 100 g aluminum) were dispersed in 650 g isopropanol. Thereafter, 1.25 g methacryloxypropyltrimethoxysilane was added and the mixture was heated to 90° C. and stirred at this temperature for 1 h. Thereafter, a mixture consisting of: 2.3 g dimethyl 2,2'-azobis (2-methylpropionate) (trade name V 601; obtainable from WAKO Chemicals GmbH, Fuggerstraβe 12, 41468 Neuss), 21.9 g trimethylolpropane trimethacrylate and 7.25 g methacryloxypropyltrimethoxysilane, topped up to a volume of 180 ml with isopropanol, was metered in over a period of 3 h. Stirring was carried out at 90° C. for a further 3 h, and the product was isolated, dried and sieved with a sieve of 71-μm mesh width.

| Experiment no. | $SiO_2$ content | Plastic content | Ratio $SiO_2:Al_2O_3$ |
|---|---|---|---|
| Example 6b | 12 wt.-% | 26.1 wt.-% | 1:4.62 |

Example 7

Wet-Chemical Oxidation and Metal Oxide Coating

Comparison Example 7a 286 g of an aluminum effect pigment-white spirit paste ($D_{50}$: 15 μm; 70.0 wt.-% solids content, 30 wt.-% white spirit, corresponds to 200 g aluminum effect pigment) was dispersed in 850 g isopropanol and stirred for 30 min. 110 g water and 10 g triethylamine were then added and heated to 60° C. for 7 h. The metal oxide layer (silicon oxide layer) was subsequently applied to the reaction product, using 94.5 g tetraethoxysilane (TEOS) and 39 g water, wherein the reaction mixture was heated to 75° C. over 4 hours.

Organic Polymer Coating

Example 7b According to the Invention 178 g of the abovementioned wet-chemically oxidized aluminum effect pigments coated with silicon oxide (having a solids content of 56 wt.-%, corresponds to 100 g aluminum) were dispersed in 650 g isopropanol. Thereafter, 1.25 g methacryloxypropyltrimethoxysilane was added and the mixture was heated to 90° C. and stirred at this temperature for 1 h. Thereafter, a mixture consisting of: 2.3 g dimethyl 2,2'-azobis (2-methylpropionate) (trade name V 601; obtainable from WAKO Chemicals GmbH, Fuggerstraβe 12, 41468 Neuss), 21.89 g trimethylolpropane trimethacrylate and 7.25 g methacryloxypropyltrimethoxysilane, topped up to a volume of 180 ml with isopropanol, was metered in over a period of 3 h. Stirring was carried out at 90° C. for a further 3 h, and the product was isolated, dried and sieved with a sieve of 71-μm mesh width.

| Experiment no. | $SiO_2$ content | Plastic content | Ratio $SiO_2:Al_2O_3$ |
|---|---|---|---|
| Example 7b | 15.7 wt.-% | 26.1 wt.-% | 1:3.31 |

Application Example 1

After-Oxidation

Aluminum effect pigments wet-chemically oxidized according to comparison example 1a without a silicon oxide coating and the pigments according to the invention according to Example 1b were stored at room temperature for 6 months. After this, the pigments, which initially were very similar in color, showed significant differences in their coloration. Comparison with analogously produced, new pigment batches showed that the pigments according to the invention had no noticeable discoloration, while the intrinsic color of the uncoated, wet-chemically oxidized aluminum effect pigments had changed significantly.

Application Example 2

Powder Coating

Application Example 2a

Applicability

The respective effect pigment was incorporated together with a powder coating AL 96 (DuPont) and with 0.2% Aeroxide Alu C (Evonik) or Acematt OK 412 (Evonik) by means of a ThermoMix (Vorwerk) at level 4 for 4 minutes. The level of pigmentation was 3.0 wt.-%.

The total amount of powder coating in the mixer was 300 g plus 0.6 g Aeroxide Alu C or Acematt OK 412. Aeroxide Alu C is a flow agent consisting of $Al_2O_3$ particles. Acematt OK 412 is a flow agent based on silica. The powder coatings were applied using the OptiSelect (ITWGema) in a commercially available powder coating booth. For evaluation of the application properties, application was carried out for 10 seconds at 100 kV and 100 μA, coating of the substrate was then carried out and the adhesions to the electrodes and to the baffle plate were then evaluated by comparison. A conclusion regarding the long-term behavior of the pigments during practice-oriented varnishing can be obtained from this method. The spray pattern was furthermore evaluated with the aid of the stoved powder coating. Attention was paid above all to the course, thus the smoothness of the surface structure, as well as to black, microscopically small defects, so-called black spots. Areas on the powder coating surface which are brought about by an inhomogeneous distribution of effect pigments are called black spots. Since these phenomena are in the macroscopic range, evaluation of this phenomenon is by assessment with the eye. Very smooth structures having a very smooth course without black spot phenomena are preferred in particular.

The application behavior, the presence of black spots and the structure or course of the powder coatings were evaluated visually.

As pigments, aluminum effect pigments were applied here before (application comparison example (ACE) 2.1) and after (ACE 2.2 and ACE 2.3) the wet-chemical oxidation according to comparison example (CE) 3a (without SiO₂ coating). Furthermore, the pigments according to the invention according to Example 3b (application example (AE) 2.4) and Example 4b (AE 2.5 and AE 2.6) were applied.

TABLE A2-1

Application examples powder coating - Applicability

| Example | Pigment | Flow agent | Result |
|---|---|---|---|
| ACE 2.1 | Aluminum effect pigments | Acematt OK 412 | readily applicable |
| ACE 2.2 | Wet-chemically oxidized aluminum effect pigments according to CE 3a | Acematt OK 412 | very strong adhesions |
| ACE 2.3 | Wet-chemically oxidized aluminum effect pigments according to CE 3a | Aeroxide Alu C | slight adhesions |
| AE 2.4 | Example 3b | Acematt OK 412 | readily applicable |
| AE 2.5 | Example 4b | Acematt OK 412 | readily applicable |
| AE 2.6 | Example 4b | Aeroxide Alu C | readily applicable |

AE: Application example
ACE: Application comparison example

Application Example 2b

Chemicals Test

The coated test sheet was brought into a horizontal position. 5 drops of 10% HCl were applied with exposure times of 180, 150, 120, 90 and 60 min. 5 drops of 1 M NaOH were furthermore applied with exposure times of 180, 120, 60, 30 and 15 min.

Thereafter, the drops were removed with water and the formerly covered surfaces were compared visually with the uncovered surfaces. A rating scale of 0-3 (for each individual point) was used here (0=no attack, 3=maximum decomposition of pigments). The points determined were then totaled.

TABLE A2-2

Application examples powder coating - Chemicals test

| Experiment no. | Chemicals test |
|---|---|
| Example 1b | 0 |
| Comparison example 2a | 9 |
| Example 2b | 0 |
| Example 3b | 0 |
| Example 4b | 0 |
| Example 6b | 0 |
| Example 7b | 0 |

Application Example 3

Wet Varnish

Application Example 3a

Chemicals Test

Aluminum effect pigments wet-chemically oxidized according to comparison example 5a without a silicon oxide coating, aluminum effect pigments according to comparison example 5a with a silicon oxide coating and the aluminum effect pigments according to the invention according to Example 5b were applied to a glass carrier in a water varnish (ZW-42-11000-01, BASF SE). After curing of the varnish, the coated test sheet was brought into a horizontal position. 5 drops of 10% HCl were applied with exposure times of 180, 150, 120, 90 and 60 min. 5 drops of 1 M NaOH were furthermore applied with exposure times of 180, 120, 60, 30 and 15 min.

Thereafter, the drops were removed with water and the formerly covered surfaces were compared visually with the uncovered surfaces. A rating scale of 0-3 (for each individual point) was used here (0=no attack, 3=maximum decomposition of pigments). The points determined were then totaled.

TABLE A3-1

Application examples wet varnish - chemicals test

| Experiment no. | Chemicals test |
|---|---|
| Aluminum effect pigments wet-chemically oxidized according to comparison example 5a (without an SiO₂ coating) | 19 |
| Comparison example 5a | 6 |
| Example 5b | 1 |

Application Example 3b

Spectrometry

Aluminum effect pigments wet-chemically oxidized according to comparison example 4a without a silicon oxide coating and the aluminum effect pigments according to the invention according to Example 4b were applied to a glass carrier in a water varnish (ZW-42-11000-01, BASF SE). After curing of the varnish, 10% HCl solution and at another place 1 molar NaOH solution is applied. After 3 h the colorimetry of the non-exposed surface, the surface treated by means of HCl solution and the surface treated by means of NaOH solution is determined with the aid of a Minolta CM-700d spectrophotometer.

TABLE A3-2

Application examples wet varnish - Spectrometry

| | Aluminum effect pigments wet-chemically oxidized according to CE 4a | | | Example 4b | | |
|---|---|---|---|---|---|---|
| | non-exposed | HCl | NaOH | non-exposed | HCl | NaOH |
| L | 79.99 | 64.73 | 77.13 | 78.76 | 78.22 | 78.86 |
| a | −0.17 | 0.69 | −0.02 | −0.20 | −0.18 | −0.20 |
| b | 7.20 | 6.69 | 7.18 | 7.08 | 7.08 | 7.10 |
| ΔE | | 15.29 | 2.86 | | 0.54 | 0.10 |

CE: Comparison example

While the color of the pigments according to the invention is almost unchanged as a consequence of the action of hydrochloric acid and sodium hydroxide solution, the color in the case of the wet-chemically oxidized aluminum effect pigments shows a serious deviation in the color values. The pigments according to the invention thus show a significantly better color stability even under very aggressive conditions.

Application Example 4

Cosmetic Formulations a. Body Lotion Water-in-Silicone

TABLE A4-1

Application example - Body lotion water-in-silicone

| INCI name | Product name | Wt.-% | Manufacturer/Supplier |
|---|---|---|---|
| Phase A | | | |
| Cyclopentasiloxane (and) Dimethiconol | Dow Corning 1501 | 11.20 | Dow Corning |
| Cyclopentasiloxane | Xiameter PMX-0245 Cyclosiloxane | 5.75 | Dow Corning |
| Cyclopentasiloxane (and) PEG/PPG-18/18 Dimethicone | Dow Corning 5225 C | 13.80 | Dow Corning |
| C 30-45 Alkyl Methicone | Dow Corning Cosmetic Wax AMS-C30 | 3.45 | Dow Corning |
| Aluminum effect pigments according to the invention according to Example 1b | | 1.00 | |
| Phase B | | | |
| Polysorbate 20 | Tween 20 | 0.60 | Croda |
| Phenoxyethanol (and) Methylparaben (and) Ethylparaben (and) Butylparaben (and) Propylparaben (and) Isobutylparaben | Uniphen P-23 | 0.35 | Induchem |
| Sodium Chloride | Sodium chloride | 0.75 | VWR |
| Aqua | Water | 63.10 | |

The aluminum effect pigment according to the invention can be used in a range of from 0.2 to 2.5 wt.-%, relative to the total weight of the formulation. The balance can be made up with water.

Phase A was mixed and heated to 75° C., phase B was heated to 70° C. after mixing, then phase B was slowly added to phase A accompanied by homogenization. The emulsion was cooled, accompanied by stirring, and poured into an appropriate container.

b. Cream Eyeshadow

TABLE A4-2

Application example - Cream eyeshadow

| INCI Name | Product name | Wt.-% | Manufacturer/Supplier |
|---|---|---|---|
| Phase A | | | |
| Castor Oil | Castor oil | 43.70 | Honeywell Riedel-de Haen |
| Ethylhexyl Palmitate | Cegesoft C24 | 6.00 | Cognis |
| Cocos Nucifera (Coconut) Oil | Lipovol C-76 | 7.00 | Lipo Chemicals |
| Cera Alba | Ewacera 12 | 6.00 | H. Erhard Wagner |
| Isopropyl Lanolate | Ewalan IP | 5.00 | H. Erhard Wagner |
| Persea Gratissima (Avocado) Oil and Hydrogenated Vegetable Oil | Avocado Butter | 7.00 | Impag |
| Magnesium Stearate | Magnesium stearate | 3.00 | Sigma-Aldrich |
| Bis-Hydroxyethoxypropyl Dimethicone | Dow Corning 5562 Carbinol Fluid | 7.00 | Dow Corning |
| Dimethicone/Vinyl Dimethicone Crosspolymer and Silica | Dow Corning 9701 Cosmetic Powder | 5.00 | Dow Corning |
| Phenoxyethanol (and) Methylparaben (and) Ethylparaben (and) Butylparaben (and) Propylparaben (and) Isobutylparaben | Uniphen P-23 | 0.30 | Induchem |
| Phase B | | | |
| Aluminium effect pigments according to the invention according to Example 1b | | 10.00 | |

The aluminum effect pigment according to the invention can be used in a range of from 5 to 22.0 wt.-%, relative to the total weight of the formulation. The balance can be made up with Castor Oil.

Phase A was mixed and heated to 85° C., then phase B was added to phase A, accompanied by stirring. After being poured into a corresponding container, the mixture is cooled to room temperature.

c. Shower Gel

TABLE A4-3

Application example - Shower gel

| INCI Name | Product name | Wt.-% | Manufacturer/Supplier |
|---|---|---|---|
| Phase A | | | |
| Aluminum effect pigments according to the invention according to Example 1b | | 0.50 | |
| Aqua | Water | 58.10 | |
| Acrylates Copolymer | Carbopol Aqua SF-1 | 5.50 | Lubrizol |
| Phase B | | | |
| Sodium Hydroxide | NaOH (10 wt.-%) | 1.50 | |
| Phase C | | | |
| Sodium Laureth Sulfate | Texapon NSO | 22.00 | Cognis |
| Cocamidopropyl Betaine | Tego Betain F 50 | 6.00 | Evonik |
| PEG-7 Glyceryl Cocoate | Emanon HE | 2.00 | Kao Corp. |
| Disodium Laureth Sulfosuccinate | Setacin 103 Spezial | 2.00 | Zschimmer & Schwarz |
| Phase D | | | |
| Phenoxyethanol (and) Piroctone Olamine | Nipaguard PO 5 | 0.60 | Clariant |
| Fragrance | Water Lily OA | 0.20 | Bell Flavors and Fragrances |
| Sodium Chloride | Sodium chloride | 1.60 | VWR |

The aluminum effect pigment according to the invention can be used in a range of from 0.01 to 1.0 wt.-%, relative to the total weight of the formulation. The balance can be made up with water.

Phase A was mixed and stirred. Thereafter, phase B was added and the mixture was stirred until a homogeneous appearance was achieved. Phase C was weighed out separately, mixed and added to phase AB. The mixture can then be stirred again and phase D was added individually.

d. Pressed Eyeshadow

TABLE A4-4

Application example - Pressed eyeshadow

| INCI Name | Product name | Wt.-% | Manufacturer/Supplier |
|---|---|---|---|
| Phase A | | | |
| Mica | Silk Mica | 17.00 | VWR |
| Boron Nitride | Softouch CCS 102 | 2.50 | Momentive |
| Zinc Stearate | Zinc stearate | 7.00 | VWR |
| Talc | Talcum powder | 43.50 | Sigma-Aldrich |
| | Aluminium effect pigments according to the invention according to Example 1b | 20.00 | |
| Phase B | | | |
| Dimethicone | Xiameter PMX-200 Silicone Fluid 5cs | 5.00 | Dow Corning |
| Cyclopentasiloxane (and) Dimethicone Crosspolymer | Dow Corning 9040 Elastomer | 5.00 | Dow Corning |

The pigment can be used in a range of from 5.0 to 40.0 wt.-%, relative to the total weight of the formulation. The balance can be made up with talc.

Phase A was mixed for 30 s at 2,500 rpm in a high-speed mixer. Phase B was then added and the mixture was mixed in the same mixer for 60 s at 3,000 rpm. Lastly, the powder mixture is pressed into shape by means of an eyeshadow press at 150 bar for 30 s.

e. Hair Mascara

TABLE A4-5

Application example - Hair mascara

| INCI Name | Product name | Wt.-% | Manufacturer/Supplier |
|---|---|---|---|
| Phase A | | | |
| Polyquaternium-16 | Luviquat FC 905 (Luviquat Excellence) | 2.70 | BASF |
| Propylene Glycol | 1,2-Propanediol | 1.80 | VWR |
| Methylparaben | Methyl 4-hydroxybenzoate | 0.20 | Sigma-Aldrich |
| Aqua | Water | 64.45 | |
| Phase B | | | |
| Cetearyl Alcohol | Lanette O | 5.00 | Cognis |
| Dimethicone | Xiameter PMX-200 Silicone Fluid 350cs | 1.00 | Dow Corning |
| Ceteareth-25 | Cremophor A 25 | 2.00 | BASF |
| Propylparaben | Propyl 4-hydroxybenzoate | 0.10 | Sigma-Aldrich |
| Phase C | | | |
| Hydroxypropylcellulose | Klucel G | 0.50 | Ashland |
| Magnesium Aluminium Silicate | Veegum HV | 0.50 | R. T. Vanderbilt |
| Aqua | Water | 19.00 | |

TABLE A4-5-continued

Application example - Hair mascara

| INCI Name | Product name | Wt.-% | Manufacturer/Supplier |
|---|---|---|---|
| Phase D | | | |
| | Aluminium effect pigments according to the invention according to Example 1b | 2.50 | |
| Phenoxyethanol (and) Methylparaben (and) Butylparaben (and) Ethylparaben (and) Propylparaben (and) Isobutylparaben | Phenonip | 0.20 | Clariant |
| Fragrance | Blue Shadow OKO | 0.05 | Bell Flavors and Fragrances |

The pigment can be used in a range of from 1.0 to 10.0 wt.-%, relative to the total weight of the formulation. The balance can be made up with the water from phase A.

Phase A and phase B were heated separately to 80° C., then phase B was slowly added to phase A. In a separate vessel, Klucel and Veegum were added to the water of phase C. Phase AB was then cooled to 40° C., and during the cooling phases C and D were added, accompanied by stirring.

f. Hair Gel

TABLE A4-6

Application example - Hair gel

| INCI Name | Product name | Wt.-% | Manufacturer/Supplier |
|---|---|---|---|
| Phase A | | | |
| | Aluminum effect pigments according to the invention according to Example 1b | 0.10 | |
| Ammonium Acryloyldimethyltaurate/VP Copolymer | Aristoflex AVC | 1.40 | Clariant |
| Citric Acid | Citric acid | 0.10 | VWR |
| Aqua | Water | 55.10 | |
| Phase B | | | |
| PVP | Luviskol K 30 Powder | 1.50 | BASF |
| Propylene Glycol, Diazolidinyl, Urea, Methylparaben, Propylparaben | Germaben II | 0.20 | International Speciality Products |
| Triethanolamine | Triethanolamine | 1.20 | VWR |
| Water | Water | 40.40 | |

The pigment can be used in a range of from 0.01 to 2.0 wt.-%, relative to the total weight of the formulation. The balance can be made up with water.

The pigment was stirred with water from phase A, Aristoflex AVC and Citric Acid were added, accompanied by stirring, and mixed at a speed of 800 rpm for 15 minutes. Phase B was dissolved until a homogeneous solution formed, then phase B was added to phase A and mixed.

g. Body Powder

TABLE A4-7

Application example - Body powder

| INCI Name | Product name | Wt.-% | Manufacturer/Supplier |
|---|---|---|---|
| Phase A | | | |
| Mica | Silk Mica | 58.70 | VWR |
| Talc | Talcum powder | 18.00 | Sigma-Aldrich |
| Boron Nitride | Softouch CCS 102 | 5.00 | Advanced Ceramics |
| Nylon-12 | Orgasol 2002 D/Nat | 8.00 | Arkema |
| Magnesium Stearate | Magnesium stearate | 6.00 | Sigma-Aldrich |
| Methylparaben, Propylparaben | Rokonsal SSH-1 | 0.30 | ISP Biochema |
| | Aluminium effect pigments according to the invention according to Example 1b | 2.00 | |
| Phase B | | | |
| Tridecyl Stearate (and) Tridecyl Trimellitate (and) Dipentaerythrityl Hexacaprylate/Hexacaprate | Lipovol MOS-130 | 2.00 | Lipo Chemicals |

The pigment can be used in a range of from 0.2 to 5.0 wt.-%, relative to the total weight of the formulation. The balance can be made up with Silk Mica.

Phase A was mixed, then phase B was added to phase A and the mixture was then poured into a suitable vessel.

h. Lip Gloss

TABLE A4-8

Application example - Lip gloss

| INCI Name | Product name | Wt.-% | Manufacturer/Supplier |
|---|---|---|---|
| Phase A | | | |
| Hydrogenated Polyisobutene (and) Ethylene/Propylene/Styrene Copolymer (and) Butylene/Ethylene/Styrene Copolymer | Versagel ME 750 | 79.00 | Calumet Penreco |
| *Simmondsia Chinensis* (Jojoba) Seed Oil | Jojoba Oil - Natural/Golden | 2.00 | BioChemica |
| Caprylyl Trimethicone | Silcare Silicone 31M50 | 7.00 | Clariant |
| Stearyl Dimethicone | Silcare Silicone 41M65 | 3.20 | Clariant |
| Hydrogenated Polydecene | Nexbase 2002 | 4.00 | Jan Dekker |
| Isopropyl Myristate | Isopropyl myristate | 4.50 | VWR |
| Phase B | | | |
| | Aluminium effect pigments according to the invention according to Example 1b | 0.10 | |
| Propylparaben | Propyl 4-hydroxybenzoate | 0.20 | Sigma-Aldrich |

The pigment can be used in a range of from 0.10 to 8.00 wt.-%, relative to the total weight of the formulation. The balance can be made up with Versagel ME 750.

Phase A was heated to 85° C., then the constituents of phase B were added individually to phase A, stirred until a uniform consistency formed and then poured into a lip gloss vessel.

i. Lip Liner

TABLE A4-9

Application example - Lip liner

| INCI Name | Product name | Wt.-% | Manufacturer/Supplier |
|---|---|---|---|
| Phase A | | | |
| Hydrogenated Coco-Glycerides | Softisan 100 | 12.35 | Sasol Wax |
| Candelilla Cera | Ewacera 42 | 14.00 | H. Erhard Wagner |
| Magnesium Stearate | Magnesium stearate | 6.00 | Sigma-Aldrich |
| Stearic Acid | Kortacid 1895 | 8.50 | Akzo Nobel |
| Hydrogenated Coconut Oil | Lipex 401 | 8.00 | Aarhus Karlshamn |
| Cetyl Palmitate | Kahlwax 7157 | 7.00 | Kahl |
| Caprylic/Capric Triglyceride | Liponate GC-K | 3.60 | Lipo Chemicals |
| Soybean Glycerides (and) *Butyrospermum Parkii* | Lipex L'sens | 15.00 | Aarhus Karlshamn |
| Tocopheryl Acetate | dl-alpha-Tocopheryl acetate | 0.25 | Jan Dekker |
| Methylparaben; Propylparaben | Rokonsal SSH-1 | 0.30 | ISP Biochema |
| Phase B | | | |
| | Aluminium effect pigments according to the invention according to Example 1b | 25.00 | |

The pigment can be used in a range of from 15 to 25 wt.-%, relative to the total weight of the formulation. Alternatively, further color and/or effect pigments can be added in addition to the pigment. However, the maximum level of pigmentation should not be exceeded.

Phase A was heated to 85° C. and phase B was then added to phase A, accompanied by stirring, until a uniform material resulted. Thereafter, the mixture was poured hot into a stick mold.

j. Lipstick

TABLE A4-10

Application example - Lipstick

| INCI Name | Product name | Wt.-% | Manufacturer/Supplier |
|---|---|---|---|
| Phase A | | | |
| Carnauba Wax | Ewacera 34 | 4.50 | H. Erhard Wagner |
| Cera Alba | Ewacera 12 | 3.50 | H. Erhard Wagner |
| Candelilla Cera Extract | Ewacera 42 | 4.00 | H. Erhard Wagner |
| Microcrystalline Wax | TeCero-Wax 1030 K | 7.20 | TH.C. Tromm |
| Cetyl Palmitate | Kahlwax 7157 | 2.00 | Kahl |
| Hydrogenated Coco-Glycerides | Softisan 100 | 5.00 | Sasol Wax |
| Petrolatum | Penreco Blond | 5.80 | Calumet Penreco |
| Cetearyl Ethylhexanoate | Luvitol EHO | 10.70 | BASF |
| Tocopheryl Acetate | dl-alpha-Tocopheryl acetate | 0.50 | Jan Dekker |
| Castor Oil | Castor oil | 46.60 | Honeywell Riedel-de Haen |

TABLE A4-10-continued

Application example - Lipstick

| INCI Name | Product name | Wt.-% | Manufacturer/Supplier |
|---|---|---|---|
| Phase B | | | |
| | Aluminium effect pigments according to the invention according to Example 1b | 10.00 | |
| Methylparaben, Propylparaben | Rokonsal SSH-1 | 0.20 | ISP Biochema |

The pigment can be used in a range of from 0.5 to 21.0 wt.-%, relative to the total weight of the formulation. The balance can be made up with Castor Oil.

Phase A was heated to 85° C., then phase B was added to phase A and mixed. This mixture was then poured into a lipstick mold at a temperature of 75° C.

k. Liquid Eyeliner

TABLE A4-11

Application example - Liquid eyeliner

| INCI Name | Product name | Wt.-% | Manufacturer/Supplier |
|---|---|---|---|
| Phase A | | | |
| Aqua | Water | 66.70 | |
| Water/carbon black dispersion | MBD 201 | 3.00 | Geotech |
| Acrylates Copolymer | Covacryl E14 | 10.00 | LCW |
| Magnesium Aluminium Silicate | Veegum HV | 1.00 | C. H. Erbslöh |
| Phase B | | | |
| Propylene Glycol | 1,2-Propanediol | 3.00 | VWR |
| Triethanolamine | Triethanolamine | 1.40 | VWR |
| Phase C | | | |
| Xanthan Gum | Keltrol CG-T | 0.30 | CP Kelco |
| Phase D | | | |
| | Aluminium effect pigments according to the invention according to Example 1b | 3.00 | |
| Mica | Silk Mica | 2.00 | VWR |
| Phase E | | | |
| Stearic Acid | Kortacid 1895 | 2.80 | Akzo Nobel |
| Glyceryl Stearate | Aldo MS K FG | 0.80 | Lonza |
| Oleyl Alcohol | HD-Ocenol 90/95 V | 0.50 | Cognis |
| Phenoxyethanol (and) Methylparaben (and) Ethylparaben (and) Butylparaben (and) Propylparaben (and) Isobutylparaben | Uniphen P-23 | 0.50 | Induchem |
| Phase F | | | |
| Dimethicone (and) Trisiloxane | Xiameter PMX-1184 Silicone Fluid | 5.00 | Dow Corning |

The pigment can be used in a range of from 0.5 to 8.0 wt.-%, relative to the total weight of the formulation. The balance can be made up with water.

Veegum was dispersed in phase A and stirred for 15 minutes, thereafter phase B was added to phase A, then phase C was added to phase AB and stirred again for 10 minutes. Phase D was then added to phase ABC and heated to 75° C. Phase E was now likewise heated to 75° C. and added to phase ABCD. After cooling to 60° C., phase F was added and the mixture poured into a suitable vessel.

l. Mousse

TABLE A4-12

Application example - Mousse

| INCI Name | Product name | Wt.-% | Manufacturer/Supplier |
|---|---|---|---|
| Phase A | | | |
| Cyclopentasiloxane | Xiameter PMX-0245 Cyclosiloxane | 8.60 | Dow Corning |
| Hydrogenated Polyisobutene | MC 30 | 4.00 | www.sophim.com |
| Dimethicone (and) Dimethicone Crosspolymer | Dow Corning 9041 Silicone Elastomer Blend | 37.14 | Dow Corning |
| Squalane | Squalane | 5.74 | Impag |
| Isononyl Isononanoate | Dermol 99 | 10.16 | Alzo International |
| Hydrogenated Jojoba Oil | Jojoba Butter LM | 2.15 | Desert Whale |
| Hydrogenated Jojoba Oil | Jojoba Butter HM | 1.00 | Desert Whale |
| C30-45 Alkyl Methicone (and) C30-45 Olefin | Dow Corning AMS-C30 Cosmetic Wax | 1.15 | Dow Corning |
| Stearyl Dimethicone | Dow Corning 2503 Cosmetic Wax | 0.47 | Dow Corning |
| Cyclopentasiloxane (and) Polypropylsilsesquioxane | Dow Corning 670 Fluid | 5.00 | Dow Corning |
| Phase B | | | |
| Dimethicone/Vinyl Dimethicone Crosspolymer | Dow Corning 9506 Powder | 16.02 | Dow Corning |
| Silica Dimethyl Silylate | Covasilic 15 | 0.17 | LCW |

TABLE A4-12-continued

Application example - Mousse

| INCI Name | Product name | Wt.-% | Manufacturer/Supplier |
|---|---|---|---|
| Talc | Talcum powder | 5.00 | Sigma-Aldrich |
| | Aluminium effect pigments according to the invention according to Example 1b | 3.00 | |
| Phase D | | | |
| Propylene Glycol, Diazolidinyl Urea, Methylparaben, Propylparaben | Germaben II | 0.40 | International Speciality Products |

The pigment can be used in a range of from 0.1 to 8.0 wt.-%, relative to the total weight of the formulation. The balance can be made up with Dow Corning 9041 Elastomer.

Phase A was mixed and heated until everything had melted. Phase B was weighed out separately and mixed for 60 s at 2,400 rpm with a high-speed mixer. Half of the melted phase A was added to phase B and mixed again in the mixer at 2,400 rpm for 30 s. The remaining part of phase B was then likewise added to phase A and mixed again at 2,400 rpm for 30 s. Lastly, phase C is added to phase AB and mixed again at 2,400 rpm for 30 s in the high-speed mixer.

m. Nail Polish

TABLE A4-13

Application example - Nail polish

| INCI Name | Product name | Wt.-% | Manufacturer/Supplier |
|---|---|---|---|
| Phase A | | | |
| | Aluminum effect pigments according to the invention according to Example 1b | 2.00 | |
| Phase B | | | |
| Butyl Acetate (and) Ethyl Acetate (and) Nitrocellulose (and) Isopropyl Alcohol | International Lacquers Nailpolish & Care Base 359 | 98.00 | International Lacquers |

The pigment can be used in a range of from 0.1 to 10.0 wt.-%, relative to the total weight of the formulation. The balance can be made up with International Lacquers Nailpolish.

Phase A and phase B were mixed and then poured into an appropriate container.

n. Nail Polish with "Soft Touch" Effect

TABLE A4-14

Application Example - Nail polish with "soft touch" effect

| INCI Name | Product name | Wt.-% | Manufacturer/Supplier |
|---|---|---|---|
| Phase A | | | |
| | Aluminum effect pigments according to the invention according to Example 1b | 2.00 | |
| | Ceraflour 913 | 5.00 | Byk Chemie |

TABLE A4-14-continued

Application Example - Nail polish with "soft touch" effect

| INCI Name | Product name | Wt.-% | Manufacturer/Supplier |
|---|---|---|---|
| Phase B | | | |
| Butyl Acetate (and) Ethyl Acetate (and) Nitrocellulose and Isopropyl Alcohol | International Lacquers Nailpolish & Care Base 359 | 93.00 | International Lacquers |

The pigment can be used in a range of from 0.1 to 10.0 wt.-%, relative to the total weight of the formulation. The balance can be made up with International Lacquers Nailpolish.

Application Example 31

Application Example—Aqueous Nail Polish

The pigment can be used in an aqueous nail polish in accordance with WO 2007/115675 A2 application example 1. The level of pigmentation here is 0.1 to 10.0 wt.-%, for example 1.5 wt.-%, relative to the total weight of the formulation.

o. Liquid Eyeshadow

TABLE A4-15

Application example - Liquid eyeshadow

| INCI Name | Product name | Wt.-% | Manufacturer/Supplier |
|---|---|---|---|
| Phase A | | | |
| Water | Water | 70.10 | |
| Glycerin | Pricerine 9090 | 6.00 | Croda |
| Phase B | | | |
| PEG-800 | Polyglycol 35000 S | 0.60 | Clariant |
| Allantoin | Allantoin | 0.30 | 3V |
| Ammonium Acryloyldimethyltaurate/VP Copolymer | Aristoflex AVC | 0.80 | Clariant |
| Acrylates Copolymer | Worlee Micromer CEK 20/50 | 5.00 | Worlee |
| Phase C | | | |
| | Aluminium effect pigments according to the invention according to Example 1b | 10.00 | |

TABLE A4-15-continued

Application example - Liquid eyeshadow

| INCI Name | Product name | Wt.-% | Manufacturer/Supplier |
|---|---|---|---|
| Divinyldimethicone/Dimethicone Copolymer C12-C13 Pareth-3,C12-C13 Pareth-23 | Dow Corning HMW 2220 Non-Ionic Emulsion | 6.00 | Dow Corning |
| Fragrance | Water Lily OA | 0.20 | Bell Flavors and Fragrances |
| Phenoxyethanol (and) Methylparaben (and) Butylparaben (and) Ethylparaben (and) Propylparaben (and) Isobutylparaben | Phenonip | 1.00 | Clariant |

The pigment can be used in a range of from 0.10 to 17.00 wt-%. The balance can be made up with water.

Phase A was stirred, then the constituents of phase B were added individually to phase A and stirred until a uniform consistency was formed. Thereafter, the constituents of phase C were added individually to phase AB and stirred until a uniform consistency formed again.

Application Example 5

Coil Coating

Application Example 5a

Chemicals Test

Aluminum effect pigments wet-chemically oxidized according to comparison example 3a without a silicon oxide coating, aluminum effect pigments according to comparison example 3a with a silicon oxide coating and the aluminum effect pigments according to the invention according to Example 3b were used in the coil coating method. 8.0 g aluminum effect pigment paste and 8.0 g Solvesso 150 were thoroughly dispersed with a spatula until the mixture was speck-free. 84.0 g polyester varnish 42-00001 (PE varnish) or 84.0 g polyvinylidene fluoride were then added and the mixture stirred, before being diluted with 5.0 g Solvesso 150. Stirring followed for 3 minutes at 500 rpm with a toothed ring stirrer. The viscosity was 100"±10 in a DIN 4 cup.

This batch of varnish was drawn down on an Alcan aluminum DIN A4 sheet (no. 11) using a spiral doctor blade. The sheet was immediately transferred into a 280° hot oven for 55 sec. Then the sheet was quenched in a water bath (RT). After 24 h at the earliest, the chemicals test was then carried out.

The coated test sheet was brought into a horizontal position. In each case one drop of hydrochloric acid (HCl) 5% and one drop of sodium hydroxide solution (NaOH) 5% was applied to the sheet. The drop size should be 20 to 25 mm in diameter. The drops were then covered with a watch glass and left to stand for 24 h. Thereafter, the drops were removed with water and the formerly covered surfaces were compared visually with the uncovered surfaces. A rating scale of 0-3 was used here (0=no attack, 3=maximum decomposition of pigments).

TABLE A5-1

Application example coil coating - Chemicals test

| Example | Pigment | | Chemicals test |
|---|---|---|---|
| ACE 5.1 | Aluminum effect pigments wet-chemically oxidized according to CE 3a without a silicon oxide coating | PE varnish | 3 |
| ACE 5.2 | CE 3a | PE varnish | 3 |
| AE 5.3 | Example 3b | PE varnish | 0 |
| ACE 5.4 | Aluminum effect pigments wet-chemically oxidized according to CE 3a without a silicon oxide coating | Polyvinylidene fluoride | 2 |
| ACE 5.5 | CE 3a | Polyvinylidene fluoride | 1 |
| AE 5.6 | Example 3b | Polyvinylidene fluoride | 0 |

AE: Application example
ACE: Application comparison example

Application Example 5b

Spectrometry

Aluminum effect pigments wet-chemically oxidized according to comparison example 3a without a silicon oxide coating, aluminum effect pigments according to comparison example 3a with a silicon oxide coating and the aluminum effect pigments according to the invention according to Example 3b were used in the coil coating method. 8.0 g aluminum effect pigment paste and 8.0 g Solvesso 150 were thoroughly dispersed with a spatula until the mixture was speck-free. 84.0 g polyvinylidene fluoride was then added and the mixture stirred, before being diluted with 5.0 g Solvesso 150. Stirring followed for 3 minutes at 500 rpm with a toothed ring stirrer. The viscosity was 100"±10 in a DIN 4 cup.

These batches of varnish were drawn down on an Alcan aluminum DIN A4 sheet (no. 11) using a spiral doctor blade. The sheets were immediately transferred into a 280° hot oven for 15 sec or 95 sec. Thereafter, the sheet was quenched in a water bath (RT). After 24 h at the earliest, the difference in the color values of the sheet heated for 15 sec and those of the sheet heated for 95 sec was determined by means of a Minolta CM-700d spectrophotometer.

TABLE A5-2

Application example coil coating - Spectrometry

| | | | Color values | |
|---|---|---|---|---|
| Example | Pigment | Varnish | Δa | Δb |
| ACE 5.7 | Aluminum effect pigments wet-chemically oxidized according to CE 3a without a silicon oxide coating | PE varnish | −0.48 | −0.87 |
| ACE 5.8 | CE 3a | PE varnish | −0.45 | −0.73 |
| AE 5.9 | Example 3b | PE varnish | −0.18 | −0.50 |

AE: Application example
ACE: Application comparison example

The wet-chemically oxidized aluminum effect pigments with and without a silicon oxide coating thus show a significant change in the color values in the direction of green (negative Δa value) and blue (negative Δb value). The pigments according to the invention, on the other hand, show a significantly higher color stability in the case of high thermal load.

The invention claimed is:

1. A coated wet-chemically oxidized aluminum effect pigment comprising:
   at least one metal oxide layer comprising at least one metal oxide which differs from aluminum oxide; and
   at least one enveloping organic polymer layer,
   wherein the weight ratio of the metal oxide of the at least one metal oxide layer to aluminum oxide in a wet-chemically produced aluminum oxide layer of uncoated wet-chemically oxidized aluminum effect pigment is in a range of from 1:1 to 1:40, and
   wherein the weight proportion of the at least one organic polymer layer is in a range of from 8 to 40 weight percent, relative to the weight of the uncoated, wet-chemically oxidized aluminum effect pigment.

2. The coated wet-chemically oxidized aluminum effect pigment according to claim 1, wherein the sum of the contents of the at least one metal oxide layer which differs from aluminum oxide and the at least one organic polymer layer is in a range of from 10 to 50 weight percent, relative to the total weight of the uncoated, wet-chemically oxidized aluminum effect pigment, and the weight ratio of the at least one metal oxide layer which differs from aluminum oxide to the at least one organic polymer layer is in a range of from 1:2 to 1:20.

3. The coated wet-chemically oxidized aluminum effect pigment according to claim 1, wherein the sum of the contents of the at least one metal oxide layer which differs from aluminum oxide and the at least one organic polymer layer is in a range of from 13 to 40 weight percent, relative to the weight of the total uncoated, wet-chemically oxidized aluminum effect pigment, and the weight ratio of the at least one metal oxide layer which differs from aluminum oxide to the at least one organic polymer layer is in a range of from 1:2.2 to 1:17.

4. The coated wet-chemically oxidized aluminum effect pigment according to claim 1, wherein the elemental aluminum content is at most 87 weight percent, relative to the total weight of the uncoated, wet-chemically oxidized aluminum effect pigment.

5. The coated wet-chemically oxidized aluminum effect pigment according to claim 1, wherein the weight proportion of the at least one metal oxide layer which differs from aluminum oxide is in a range of from 0.8 to 20 weight percent, relative to the total weight of the uncoated, wet-chemically oxidized aluminum effect pigment.

6. The coated wet-chemically oxidized aluminum effect pigment according to claim 1, wherein the at least one metal oxide layer which differs from aluminum oxide substantially consists of at least one metal oxide which is selected from the group consisting of silicon oxide, boron oxide, zirconium oxide, cerium oxide, iron oxide, titanium oxide, chromium oxide, tin oxide, molybdenum oxide, oxide hydrates thereof, hydroxides thereof and mixtures thereof.

7. The coated wet-chemically oxidized aluminum effect pigment according to claim 1, wherein the at least one metal oxide layer which differs from aluminum oxide substantially consists of silicon oxide.

8. The coated wet-chemically oxidized aluminum effect pigment according to claim 1, wherein the at least one organic polymer layer substantially consists of at least one organic, polymer which is selected from the group consisting of polyacrylate, polymethacrylate, polyacrylamide, polyacrylonitrile, polyvinyl chloride, polyvinyl acetate, polyamide, polyalkene, polydiene, polyalkyne, polyalkylene glycol, epoxy resin, polyester, polyether, polyol, polyurethane, polycarbonate, polyethylene terephthalate and mixtures thereof.

9. The coated wet-chemically oxidized aluminum effect pigment according to claim 1, further comprising a high refractive index metal chalcogenide layer.

10. The coated wet-chemically oxidized aluminum effect pigment according to claim 1, wherein the weight ratio of the metal oxide of the at least one metal oxide layer to the aluminum oxide in the wet-chemically produced aluminum oxide layer of the uncoated wet-chemically oxidized aluminum effect pigment is in a range of from 1:2 to 1:25.

11. The coated wet-chemically oxidized aluminum effect pigment according to claim 1, wherein the pigment is produced by:
   (1) wet-chemical oxidation of an aluminum effect pigment,
   (2) coating of the wet-chemically oxidized aluminum effect pigment obtained in step (1) with metal oxide which differs from aluminum oxide, wherein the weight ratio of the metal oxide, applied as at least one metal oxide layer, to the aluminum oxide layer wet-chemically produced in step (1) is in a range of from 1:1 to 1:40, and
   (3) coating of the wet-chemically oxidized aluminum effect pigment, coated with metal oxide and obtained in step (2), with at least one enveloping organic polymer layer.

12. A process for producing a pigmented plastic, cosmetic product, or coating agent, comprising introducing the coated wet-chemically oxidized aluminum effect pigment according to claim 1 into a plastic, a cosmetic product or a coating agent.

13. The process according to claim 12, wherein the coating agent is selected from the group consisting of paint, varnish, powder coating, and printer ink.

14. A pigmented coating agent comprising at least one coated wet-chemically oxidized aluminum effect pigment according to claim 1.

15. A method for the production of a coated wet-chemically oxidized aluminum effect pigment, wherein the method comprises the following steps:
   (1) wet-chemical oxidation of an aluminum effect pigment,
   (2) coating of the wet-chemically oxidized aluminum effect pigment obtained in step (1) with metal oxide which differs from aluminum oxide, wherein the weight ratio of the metal oxide, applied as at least one metal oxide layer, to the aluminum oxide layer wet-chemically produced in step (1) is in a range of from 1:1 to 1:40, and
   (3) coating of the wet-chemically oxidized aluminum effect pigment, coated with metal oxide and obtained in step (2), with at least one enveloping organic polymer layer, wherein the weight proportion of the at least one organic polymer layer is in a range of from 8 to 40 weight percent, relative to the weight of the uncoated, wet-chemically oxidized aluminum effect pigment.

16. The method according to claim 15, wherein in step (2) the metal oxide is applied with a sol-gel process.

17. The method according to claim 15, wherein the wet-chemical oxidation is carried out at pH 7 to 12 with a mixture of water and one or more water-miscible solvents.

18. A coated wet-chemically oxidized aluminum effect pigment comprising:
   at least one metal oxide layer comprising at least one metal oxide which differs from aluminum oxide; and
   at least one enveloping organic polymer layer,
   wherein the weight ratio of the metal oxide of the at least one metal oxide layer to aluminum oxide in a wet-chemically produced aluminum oxide layer of uncoated wet-chemically oxidized aluminum effect pigment is in a range of from 1:1 to 1:40, and
   wherein the sum of the contents of the at least one metal oxide layer which differs from aluminum oxide and the at least one organic polymer layer is in a range of from 10 to 50 weight percent, relative to the total weight of the uncoated, wet-chemically oxidized aluminum effect pigment, and the weight ratio of the at least one metal oxide layer which differs from aluminum oxide to the at least one organic polymer layer is in a range of from 1:2 to 1:20.

19. A method fir the production of a coated wet-chemically oxidized aluminum effect pigment, wherein the method comprises the following steps:
   (1) wet-chemical oxidation of an aluminum effect pigment,
   (2) coating of the wet-chemically oxidized aluminum effect pigment obtained in step (I) with metal oxide which differs from aluminum oxide, wherein the weight ratio of the metal oxide, applied as at least one metal oxide layer, to the aluminum oxide layer wet-chemically produced in step (1) is in a range of from 1:1 to 1:40, and
   (3) coating of the wet-chemically oxidized aluminum effect pigment, coated with metal oxide and obtained in step (2), with at least one enveloping organic polymer layer,
   wherein the sum of the contents of the at least one metal oxide layer which differs from aluminum oxide and the at least one organic polymer layer is in a range of from 10 to 50 weight percent, relative to the total weight of the uncoated, wet-chemically oxidized aluminum effect pigment, and the weight ratio of the at least one metal oxide layer which differs from aluminum oxide to the at least one organic polymer layer is in a range of from 1:2 to 1:20.

* * * * *

UNITED STATES PATENT AND TRADEMARK OFFICE
CERTIFICATE OF CORRECTION

PATENT NO. : 9,260,584 B2
APPLICATION NO. : 14/355984
DATED : February 16, 2016
INVENTOR(S) : Dirk Schumacher et al.

It is certified that error appears in the above-identified patent and that said Letters Patent is hereby corrected as shown below:

In the Claims

Column 53, Line 61, Claim 8, delete "organic," and insert -- organic --

Column 55, Line 8, Claim 19, delete "fir" and insert -- for --

Column 55, Line 13, Claim 19, delete "(I)" and insert -- (1) --

Signed and Sealed this
Fourteenth Day of June, 2016

Michelle K. Lee
*Director of the United States Patent and Trademark Office*